United States Patent
Fujihara et al.

(10) Patent No.: US 11,891,412 B2
(45) Date of Patent: Feb. 6, 2024

(54) PRODUCTION OF HIGHLY FAT-SOLUBLE PHOSPHORAMIDITE

(71) Applicant: KNC LABORATORIES CO., LTD., Kobe (JP)

(72) Inventors: Tsuyoshi Fujihara, Kobe (JP); Kenichi Nakamura, Kobe (JP); Toru Kurome, Kobe (JP); Daisuke Sasahara, Kobe (JP); Akiko Shimahara, Kobe (JP); Masahiro Neya, Kobe (JP)

(73) Assignee: KNC LABORATORIES CO., LTD., Hyogo (JP)

( * ) Notice: Subject to any disclaimer, the term of this patent is extended or adjusted under 35 U.S.C. 154(b) by 892 days.

(21) Appl. No.: 16/958,100

(22) PCT Filed: Dec. 26, 2018

(86) PCT No.: PCT/JP2018/047748
§ 371 (c)(1),
(2) Date: Sep. 17, 2020

(87) PCT Pub. No.: WO2019/131719
PCT Pub. Date: Jul. 4, 2019

(65) Prior Publication Data
US 2021/0087220 A1    Mar. 25, 2021

(30) Foreign Application Priority Data

Dec. 27, 2017  (JP) .................... 2017-252107

(51) Int. Cl.
C07H 21/04   (2006.01)

(52) U.S. Cl.
CPC .................... C07H 21/04 (2013.01)

(58) Field of Classification Search
None
See application file for complete search history.

(56) References Cited

U.S. PATENT DOCUMENTS

| | | | |
|---|---|---|---|
| 6,107,479 | A | 8/2000 | Natt et al. |
| 7,276,620 | B2 | 10/2007 | Harris et al. |
| 7,558,032 | B2 | 7/2009 | Piasecki et al. |
| 7,858,772 | B2 | 12/2010 | Gupta et al. |
| 2006/0128951 | A1 | 6/2006 | Harris et al. |
| 2007/0103823 | A1 | 5/2007 | Piasecki et al. |
| 2008/0161548 | A1 | 7/2008 | Gupta et al. |
| 2018/0264105 | A1 | 9/2018 | Kugimiya et al. |
| 2018/0282365 | A1 | 10/2018 | Hirai et al. |
| 2019/0169223 | A1 | 6/2019 | Sugawara |

FOREIGN PATENT DOCUMENTS

| | | |
|---|---|---|
| JP | 2006-512386 | 4/2006 |
| JP | 2010-24228 | 2/2010 |

(Continued)

OTHER PUBLICATIONS

Meyer, Tetrahedron Letters 47 (2006) 8867-8871. (Year: 2006).*
Supplementary Partial European Search Report in the corresponding European Patent Application No. 18895849.0, dated Aug. 27, 2021, 17 pages.
Brodersen Nicolai et al. "Nucleosides with 5'-Fixed Lipid Groups—Synthesis and Anchoring in Lipid Membranes," European Journal of Organic Chemistry, vol. 2007, No. 36, Dec. 1, 2007, pp. 6060-6069.
Gian Maria Bonora et al., "HELP (High Efficiency Liquid Phase) new oligonucleotide synthesis on soluble polymeric support", Nucleic Acids Research, 1990, vol. 18, No. 11, pp. 3155-3159.
Francesco P. Colonna et al., "Large Scale H.E.L.P. Synthesis of Oligodeoxynucleotides by the Hydroxybenzotriazole Phosphotriester Approach.", Tetrahedron Letters, 1991, vol. 32, No. 27, pp. 3251-3254.

(Continued)

*Primary Examiner* — Layla D Berry
(74) *Attorney, Agent, or Firm* — Hamre, Schumann, Mueller & Larson, P.C.

(57) ABSTRACT

The purpose of the present invention is to provide a method for purifying and preparing a highly liposoluble phosphoramidite, as well as a capping reaction using the highly liposoluble phosphoramidite compound, and as well as a method for preparing oligonucleotide by a liquid phase process using a pseudo solid phase protecting group said method comprising the capping reaction step. The present invention also provides a method for preparing a compound represented by formula (I) [wherein, $R^1$, $R^2$ and $R^3$ are defined as described in the Detailed Description], which comprises the following steps: (1) reacting an aliphatic alcohol and a trivalent phosphorus compound in organic solvent in the presence of an activator or an organic base; (2) washing the resulting reaction mixture with water in a reparatory funnel; (3) recovering the organic layer after the step (2) and concentrating it (with the proviso that the organic solvent used in the step (1) is a nitrile solvent, the steps (2) to (3) may be omitted); (4) solubilizing the resulting residue obtained in the step (3) in an aliphatic hydrocarbon solvent (with the proviso that the organic solvent used in the step (1) is an aliphatic hydrocarbon solvent, the steps (2) to (3) may be omitted); (5) washing the aliphatic hydrocarbon solution prepared in the step (4) with a nitrile solvent in a separatory funnel; (6) recovering the aliphatic hydrocarbon solution after the step (5) to obtain a solution of a phosphoramidite compound. Also the present invention provides also a solution containing highly liposoluble phosphoramidite compound obtained by the preparation method, a capping reagent comprising the same solution and optionally an additive, a capping reaction using the same capping reagent, as well as a method for preparing (oligo)nucleotide by using the pseudo solid phase protecting group, said method comprising the capping reaction step.

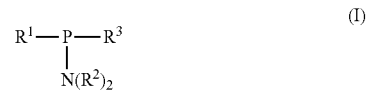

(I)

6 Claims, 2 Drawing Sheets

(56) References Cited

FOREIGN PATENT DOCUMENTS

| | | |
|---|---|---|
| JP | 2010-513358 | 4/2010 |
| JP | 2010-275254 | 12/2010 |
| JP | 2011-121881 | 6/2011 |
| WO | 1998/020018 | 5/1998 |
| WO | 2004/058779 | 7/2004 |
| WO | 2005/008859 | 1/2005 |
| WO | 2017/057540 | 4/2017 |
| WO | 2017/086397 | 5/2017 |
| WO | 2017/104836 | 6/2017 |

OTHER PUBLICATIONS

Gian Maria Bonora et al., "Large scale, liquid phase synthesis of oligonucleotides by the phosphoramidite approach", Nucleic Acids Research, 1993, vol. 21, No. 5, pp. 1213-1217.
Shokaku Kim et al., "Liquid-Phase RNA Synthesis by Using Alkyl-Chain-Soluble Support", Chem. Eur. J. 2013, 19, pp. 8615-8620.
Jared W. Rigoli et al., "Selective deacylation of peracylated ribonucleotides", Tetrahedron Letters, 2009, 50, 15, pp. 1751-1753.
Richard T. Pon et al., "Prevention of guanine modification and chain cleavage during the solid phase synthesis of oligonucleotides using phosphoramidite derivatives", Nucleic Acids Research, 1986, vol. 14, No. 16, pp. 6453-6470.
Andrei P. Guzaev, "Reactivity of 3H-1,2,4-dithiazole-3-thiones and 3H-1,2-dithiole-3-thiones as sulfurizing agents for oligonucleotide synthesis", Tetrahedron Letters, 2011, 52, 434-437.
Dong Yu et al., "Diethoxy N, N-diisopropyl Phosphoramidite as an Improved Capping Reagent in the Synthesis of Oligonucleotides Using Phosphoramidite Chemistry", Tetrahedron Letters, 1994, vol. 35, No. 46, pp. 8565-8568.
François Natt et al., "Lipocap: a Lipophilic Phosphoramidite-based Capping Reagent", Tetrahedron 1997, vol. 53, No. 28, pp. 9629-9636.
Michael J. Palte et al., "Interaction of Nucleic Acids with the Glycocalyx", Journal of the American Chemical Society, Mar. 8, 2012, 134, 6218-6223.
International Search Report of PCT/JP2018/047748, dated Mar. 26, 2019, 4 pages.
International Preliminary Report on Patentability of PCT/JP2018/047748, dated Jun. 30, 2020, 8 pages.

* cited by examiner

[FIGURE 1]
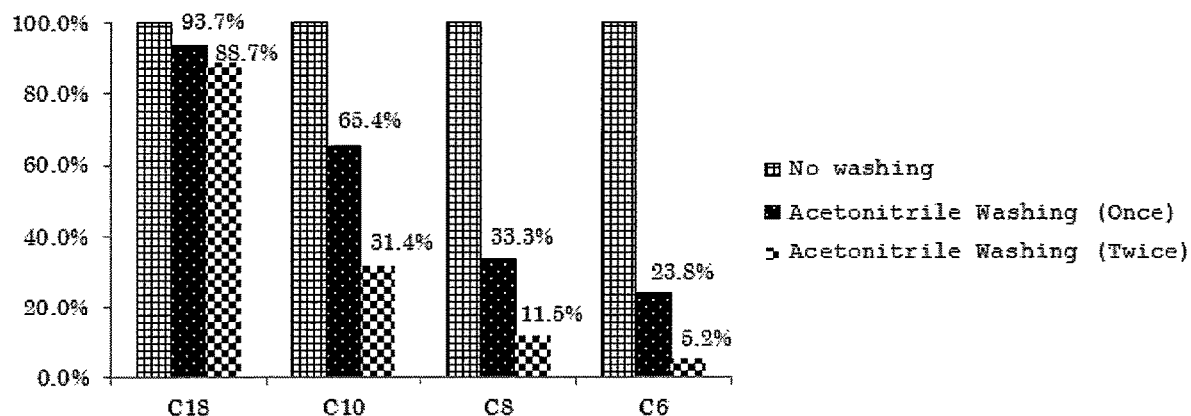

[FIGURE 2]
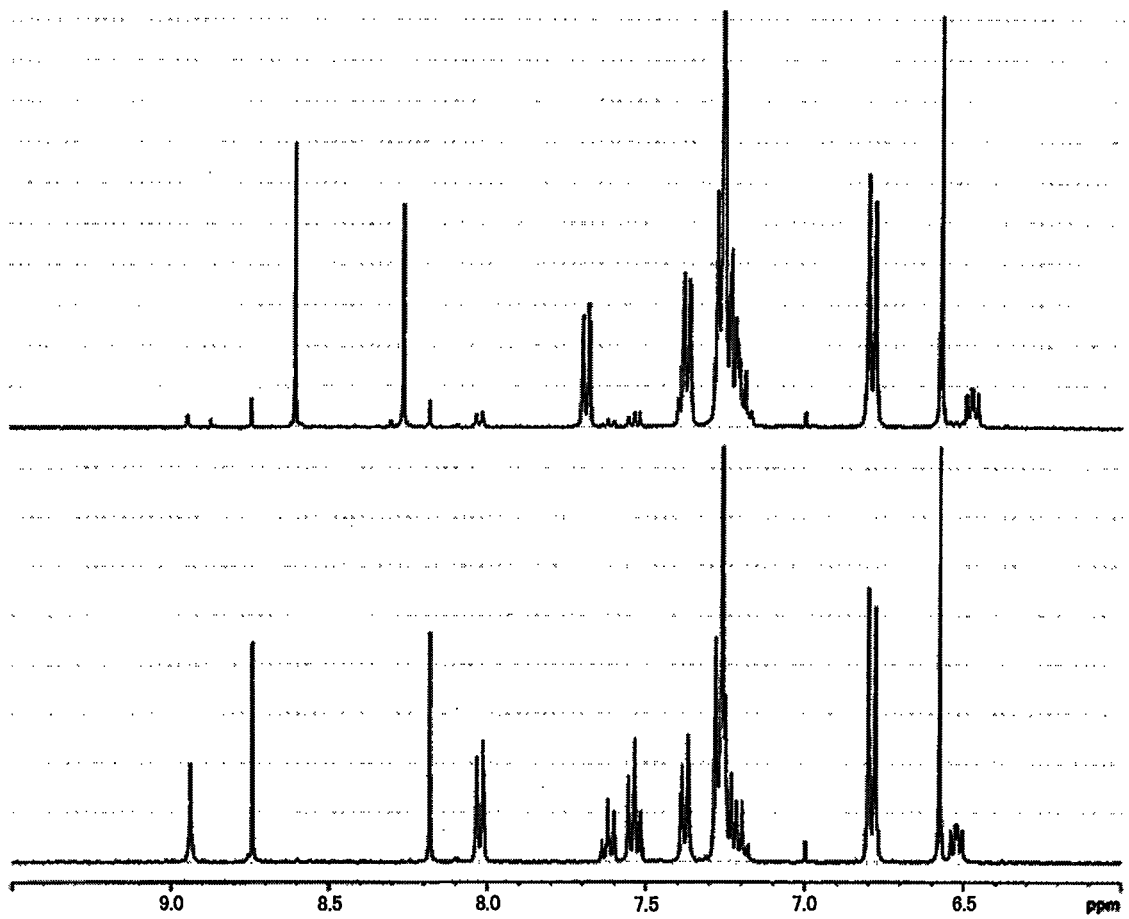

PRODUCTION OF HIGHLY FAT-SOLUBLE PHOSPHORAMIDITE

TECHNICAL FIELD

The present invention relates to a highly liposoluble phosphoramidite. More specifically, the present invention also relates to a method for purifying and preparing a highly liposoluble phosphoramidite, as well as a capping reaction solution being a solution containing the highly liposoluble phosphoramidite compound and a capping reaction using the capping reaction solution, as well as a method for preparing oligonucleotide by a liquid phase process comprising the capping reaction step.

BACKGROUND ART

In recent years, researches using synthetic oligonucleotide have been actively conducted, and as a result, oligo nucleic acid drugs have been put on the market. On the other hand, a synthetic method capable of synthesizing high-purity oligonucleotides on a large scale is required.

Examples of a preparation method of oligonucleotide include a phosphotriester method, a H-phosphonate method, a phosphoramidite method, and the like, and currently, a solid-phase synthesis (solid phase method) using the phosphoramidite method is most widely used. As the synthesis of oligonucleotide, an approach for sequentially linking nucleotides as raw materials, an approach for repeating the linking of building blocks of about 2 to 3 nucleotides (blockmer synthesis method), an approach by linking of about 10 bases of oligonucleotide (fragment condensation method) or the like is known.

Although a solid phase synthesis (solid phase process) is advantageous in terms of synthesis speed, such as using an automatic synthesizer, there are the following some disadvantages, for example, a scale-up of the synthesis is limited, and excessive amounts of reaction reagents and reaction raw materials are required, and it is difficult to monitor the progress of the reaction, especially in the halfway stage during the synthetic reaction and to analyze an intermediate compound.

Whilst, since the procedure for the synthesis of oligonucleotide by liquid phase process is complicated and the yield is low, there are some disadvantages, for example, it is difficult to synthesize an oligonucleotide having a high degree of polymerization in large amount and rapidly.

In recent years, an oligonucleotide synthesis method using polyethylene glycol (MPEG) has been reported with the aim of eliminating each of a disadvantage on the solid phase process and the liquid phase process respectively (see Non-patent literatures 1 to 3). Although a synthetic example of oligonucleotide up to about 20-mer has been reported by the method, there were some problems that a crystallization isolation procedure and a recrystallization at each step in the elongation cycle was required, and also was complicated.

Also, in the liquid phase preparation method, a preparation of a nucleotide using a nucleoside in which a particular hydrophobic group is adopted as a soluble resin which mimics a resin used in solid phase synthesis and to which the hydrophobic group (hereinafter, sometimes referred to also as "pseudo solid phase protecting group") is attached, that is, a hydrophobic bond-bounded nucleoside (see Patent literature 1, and Non-Patent Literature 4). A preparation of a 21-mer oligonucleotide has been reported by the above method. However, the method is required for a crystallization—isolation procedure in each step of a step of a deprotection reaction for 5'-protecting group, a step of a coupling reaction, and a step of an oxidative reaction, respectively, and accordingly, is complicated because of so many steps required.

In the conventional preparation method of oligonucleotide, unreacted materials such as unreacted raw materials are involved in the elongation step of oligonucleotide, and as a result, there is a problem that N−1 and N+1 by-products are formed as opposed to the desired oligonucleotide. Also it has been very difficult to distinguish and separate these by-products from the desired product. Accordingly, in the case where the synthetic oligonucleotide product is used as a nucleic acid drug, there is a demand for a preparation method by reducing a formation of these N−1 and N+1 by-products, said preparation method being capable of obtaining oligonucleotides with a purity equal to or higher than that of the oligonucleotides obtained by the conventional method.

In order to prevent a proceeding of an elongation reaction in competition with the reaction active site in the desired oligonucleotide chain in the next synthesis cycle and a production of a N−1 oligonucleotide by protecting a reaction active site in unreacted oligonucleotide chain after coupling reaction of an oligonucleotide with a nucleotide, a capping reagent is used in a solid phase preparation method.

However, as for a preparation method of oligonucleotide by a liquid phase method using a pseudo solid phase protecting group (in particular, a DNA phosphoramidite method), since it is a reaction in a liquid phase system, the reactivity such as coupling reaction is higher than that of the solid phase method, and it is not necessary to use a large excess amount of reaction raw materials and reaction reagents. Accordingly, no reagent (capping reagent) for capping an unreacted oligonucleotide chain which is used in the solid phase preparation method, is added, and accordingly, no reagent (capping reagent) for capping unreacted oligonucleotide chains, which is used in the solid-phase production method, is added, and hence, liquid-phase synthesis reaction using the capping reagent has not been reported.

The reason why a capping reagent is not used in the liquid phase method using a pseudo solid phase protecting group is also thought in addition to the above-mentioned reactivity, in particular, to be due to the following problems. In a phosphoramidite reaction which is commonly used in solid phase oligonucleotide synthesis, usually though a large excess amount of acetic anhydride and a large excess mount of bases such as imidazole derivatives are used as a capping reagent, the following problems are included: additional purification steps are required to remove these acids and bases; the property (for example, hydrophobicity) of a capping product of the unreacted oligonucleotide chain has an intermediate property between that of the oligonucleotide chain and that of the desired product of the coupling reaction; and there is a possibility that the nucleic acid base may be partially acetylated (mainly, 6-amide of adenine, 2-amide of a partial of guanine, 4-amide of a cytidine, 3-position of thymine) to form a diacyl product, which may form a reaction mixture (see Non-patent literature 5). In that case, there is a problem in which since each compound in these mixtures gives a similar reaction product in the next synthesis cycle and then produces more complicated reaction mixtures, it becomes difficult to analyze the resulting products by the usual analysis method (for example, TLC and HPLC), and which thus makes it very difficult to confirm the end point of the nucleotide coupling reaction.

However, it has been also reported that a capping step using anhydrous acetate suppress yield of a by-product of phosphoramidite and nucleic acid base (mainly, 6-carbonyl oxygen atom of guanine) in a preparation method of oligonucleotide (in particular, DNA) (see Non-Patent literature 6).

Also, in a liquid phase preparation method using a pseudo solid phase protecting group, it succeeds in improving the purity of the product by adding an organic base salt of carboxylic acid or a quench reagent such as alcohol soon after elongation reaction by phosphoramidite (see Patent literature 2). However, it can be easily predicted that it would be difficult to conduct a capping reaction using anhydrous acetate without any additional purification step because the organic base salt of a carboxylic acid or the alcohol has a reactivity with anhydrous acetate. In particular, since it has been reported that a sulfidation efficiency is reduced by using anhydrous acetate or water before the sulfidation reaction (see Non-Patent literature 7), it is essential to confirm the sulfidation efficiency in the case when the sulfidation reaction is conducted by adding an alcohol and the like.

Also a capping reagent aims to suppress a production of N−1 by-product formed in an oligonucleotide synthesis and thus improve a purity of a desired oligonucleotide product. As a capping reagent, there are also some examples using alkoxy phosphoramidite compound except for the above-mentioned anhydrous acetate. However, since the alkoxy phosphoramidite compound is extremely more expensive compared to anhydrous acetate, the primary alkoxy phosphoramidite compound having high reactivity has been used (see Patent literatures 3 and 4, as well as Non-Patent literatures 8 and 9). Also in these literatures, it has not been reported a side reaction between the primary alkoxy phosphoramidite and nucleic acid base (mainly, on 6-carbonyl oxygen of guanine).

In the case where the primary alkoxy phosphoramidite compound is used as a capping reagent, it is expected to lower the number of equivalent required due to a high reactivity thereof. However, in the case of a synthesis of oligo nucleic acid on a large scale, a significant amount of the primary alkoxy phosphoramidite compound is required, and it is required for a development of a method for preparing a high purity-alkoxy phosphoramidite compound more conveniently and more safely and on a large scale thereof.

A column purification of the primary alkoxy phosphoramidite compound having high reactivity does not use a usualy cheap amine-existing type of silica gel, but use an expensive amino silica gel (see Patent literature 5). It has been reported that a phosphorodiamidite compound which can be used as raw materials of a phosphoramidite compound is recovered by adding poor solvents (such as alcohols, hydrocarbons, nitriles) to a reaction mixture (see patent literatures 6 and 7). However, it cannot be predicted whether a similar method can be applied to the primary alkoxy phosphoramidite compound having high reactivity, and thus, it is further predicted to require for an appropriate selection of alcohol as raw material.

CITATION LIST

Patent Document

Patent Document 1: JP 2010-275254 A1
Patent Document 2: WO 2017/104836 A1
Patent Document 3: JP 2010-513358 A1
Patent Document 4: WO 2005/008859 A2
Patent Document 5: JP 2011/121881 A1
Patent Document 6: JP 2010-24228 A1
Patent Document 7: WO 2004-058779 A1

Non-Patent Document

Non-Patent Document 1: Nucleic Acids Research, 1990, 18, 3155-3159
Non-Patent Document 2: Tetrahedron Lett. 1991, 32, 27, 3251-3254
Non-Patent Document 3: Nucleic Acids Research, 1993, 21, (5) 1213-1217
Non-Patent Document 4: Chem. Eur. J. 2013, 19, 8615-8620
Non-Patent Document 5: Tetrahedron Letters, 2009, 50, 15, 1751-1753
Non-Patent Document 6: Nucleic Acids Research, 1986, 14, (16) 6453-6470
Non-Patent Document 7: Tetrahedron Lett. 2011, 52, 434-437
Non-Patent Document 8: Tetrahedron Lett. 1994, 35, 46, 8565-8568
Non-Patent Document 9: Tetrahedron 1997, 53, 28, 9629-9636

SUMMARY OF THE INVENTION

Problems to be Solved by Invention

The present invention relates to a preparation method of highly liposoluble phosphoramidite. More specifically, the present invention also provide a method of convenient purification and preparation of highly liposoluble phosphoramidite as an alkoxy phosphoramidite compound capable of using as a capping reagent in the oligonucleotide synthesis, as well as a capping reaction solution as a solution containing a highly liposoluble phosphoramidite compound obtained by the same preparation method, and a preparation method by liquid phase process using a pseudo solid phase protecting group, the method comprising a capping reaction step.

Means to Solve Problems

According to the present invention, it is found out a preparation method of preparing highly liposoluble phosphoramidite as one kind of alkoxy phosphoramidite compound which is capable of using as a capping reagent in the oligonucleotide synthesis without requiring for the such procedures as column purification, and the same compound can be conveniently purified by procedures with a separatory funnel and the like based on a selection of a kind of soluting solvent and washing solvent as well as washing order thereof, which can prepare the same compound with high purity in an industrially large scale. Also, it is found out that in the case where the solution containing the highly liposoluble phosphoramidite obtained by the preparation method is used as a capping reaction solution in a liquid phase method (in particular, a liquid phase method using a peudo solid phase protecting group), a capping reaction can be achieved, and also though a side reaction is occurred, it is found out that worked-up treatments using a nucleophile (for example, alcohol) can be conducted to suppress a yield of such a by-products. Also, throughout the synthesis of oligonucleotide, such a capping reaction and worked-up treatments thereafter does not affect any adverse effect (for example, inhibition of a reaction) on some essential steps followed by the capping reaction (oxidation reaction and/or sulfidation reaction of oligonucleotide), and thus the yield of the desired product can be improved.

That is, the present invention provides the following embodiments, however, which are not limited thereto.

(Preparation and Purification Method of Highly Liposoluble phosphoramidite)

Item [1] A method for preparing a compound represented by formula (I):

[wherein,
- $R^1$ represents an optionally substituted C6-C30 alkyloxy group, and the substituent is at least one group selected from a C1-C3 alkyl group or a C3-C6 cycloalkyl group,
- $R^2$ each independently represents an optionally substituted C1-C6 alkyl group, and the substituent is at least one group selected from a C1-C3 alkyl group or a C3-C6 cycloalkyl group, and
- $R^3$ represents an optionally substituted C6-C30 alkyloxy group, an optionally substituted C1-C8 alkyloxy group, or an optionally substituted C2-C8 alkynyloxy group, and the substituent in the optionally substituted C6-C30 alkyloxy group is at least one group selected from a C1-C3 alkyl group, or a C3-C6 cycloalkyl group, and the substituent in the optionally substituted C1-C8 alkyloxy group or the optionally substituted C2-C8 alkynyloxy group is a cyano group (CN)], which comprises the following steps:
(1) reacting an aliphatic alcohol and a trivalent phosphorus compound in organic solvent in the presence of an activator or an organic base;
(2) washing the resulting reaction mixture with water in a separatory funnel;
(3) recovering the organic layer after the step (2) and concentrating it (with the proviso that the organic solvent used in the step (1) is a nitrile solvent, the steps (2) to (3) may be omitted);
(4) solubilizing the resulting residue obtained in the step (3) in an aliphatic hydrocarbon solvent (with the proviso that the organic solvent used in the step (1) is an aliphatic hydrocarbon solvent, the steps (2) to (3) may be omitted);
(5) washing the aliphatic hydrocarbon solution prepared in the step (4) with a nitrile solvent in a separatory funnel;
(6) recovering the aliphatic hydrocarbon solution after the step (5) to obtain a solution of a phosphoramidite compound.

Item [2] The method according to Item [1] wherein the aliphatic hydrocarbon solvent used in the step (4) is at least one selected from pentane, hexane, heptane or octane, and the nitrile solvent used in the step (5) is at least one selected from acetonitrile, propionitrile, or benzonitrile.

Item [3-1] The preparation according to the Item [1] or [2] wherein $R^2$ represents an optionally substituted C1-C8 alkyloxy group, or the optionally substituted C2-C8 alkynyloxy group, and the substituent is a cyano group (CN).

Item [3-2] The preparation method according to the Item [1] or [2] wherein $R^2$ represents an optionally substituted C1-C8 alkyloxy group.

Item [3-3] The preparation method according to Item [1] to [2] wherein $R^1$ represents an optionally substituted C10-C30 primary or secondary alkyloxy group, and $R^3$ represents a —OCH$_2$CH$_2$CN, —OCH$_3$ or —OCH$_2$CH$_3$ group.

Item [4] The preparation method according to any one of Item [1] to [3] wherein each $R^2$ represents a i-propyl group.

Item [5] The preparation method according to any one of [1] to [4] wherein the compound represented by formula (I) is a compound represented by the following formula:

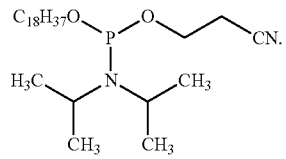

Item [6] The preparation method according to any one of [1] to [5] wherein the solution obtained in the step (6) is a solution of a substantially pure phosphoramidite compound which does not contain H-phosphonate compound and a diamidite compound.

(Capping Reaction Composition and Capping Reaction)

Item [7] A composition for capping reaction which comprises a solution containing any compound obtained by the method according to any one of the Items [1] to [6], and optionally an additive.

Item [8] A capping method which comprises a step of contacting the reaction solution obtained after the capping reaction of two or more compounds selected from nucleoside, nucleotide or oligonucleotide to the composition for capping reaction according to the Item [7], optionally in the presence of an activator.

Item [9] The capping method according to the Item [8], which further comprises optionally reacting a by-product of the capping reaction with a nucleophile after the capping reaction step, and the nucleophile is selected from alcohol, phenol, carboxylic acid, or N-alkyl hydroxylamine.

Item [10] The capping reaction according to the Item [9] which comprises a step of adding an organic base after the capping reaction step, followed by reacting with a nucleophile.

(Preparation Method of Oligonucleotide)

Item [11] A method for preparing oligonucleotide which comprises the following steps:

step (a): a n-mer wherein a pseudo solid phase protecting group is modified through a 3'-hydroxy group or a nucleic acid base and also a 5'-hydroxy group is blocked with a temporary protecting group which is removable under an acid condition (wherein n is an arbitrary integer of 1 or more), or when n is 0, a compound wherein one hydroxy group of a linker containing two hydroxy groups is modified with a pseudo solid phase protecting group and also another hydroxy group thereof is blocked with a temporary protecting group which is removable under an acid condition is reacted in a nonpolar solvent in the presence of an acid singly or in co-existence thereof with a cation scavenger to deblock the temporary protecting group of the hydroxy group, and then the compound containing the pseudo solid phase protecting group is recovered using a polar solvent (Deblocking and Crystallization Step);

step (b): after drying the recovered materials in the step (a), to the resulting residue in a non-polar solvent were added a m+1 polymerized polynucleotide wherein a 3'-hydroxy group is phosphoramidited and also a 5'-hydroxy group is protected with a temporary protecting group which is removable under an acid condition (wherein m is an arbitrary integer of 0 or more) and an activator to condense the m+1 polymerized polynucleotide to the compound obtained in the step (a) wherein a temporary protecting group of a hydroxy group is deblocked (n-polymerized polynucleotide) by a phosphite triester bond through its 5' hydroxy group of the m+1 polymerized polynucleotide (coupling step);

step (c): to a reaction solution of the step (b) is added the solution containing the highly liposoluble phosphoramidite compound obtained by the preparation method according to any one of the Items [1] to [6] or the composition for capping reaction according to the Item [7] to condense the unreacted compound in the step (b) to the highly liposoluble compound by a phosphite triester bond through its 5'-hydroxy group of the unreacted compound (capping reaction step);

step (d): a nucleophile is added to react with the by-product of capping reaction of step (c), wherein the nucleophile is selected from alcohol, phenol, carboxylic acid or N-alkyl hydroxylamine (worked-up step of capping reaction);

step (e): an oxidizing agent or a sulfidizing agent is added to the reaction solution of step (d) to convert a phosphite triester bond in the m+1+n-mer of oligonucleotide obtained in the steps (b) to (d) to a phosphate triester bond or a thiophosphate triester bond respectively (Oxidation reaction step or Sulfidation reaction step);

further optionally step (f): a polar solvent is added to the reaction solution obtained in the step (e) to precipitate out the m+1+n-polymerized oligonucleotide, and obtain the oligonucleotide by a solid-liquid separation method (Purification step);

further optionally step (g): all protecting groups in the m+1+n-polymerized oligonucleotide are removed (Deprotection Step).

(Pseudo Solid Phase Protecting Group and Nucleotide Compound Comprising the Same)

Item [12]

A pseudo solid phase protecting group represented by formula (II):

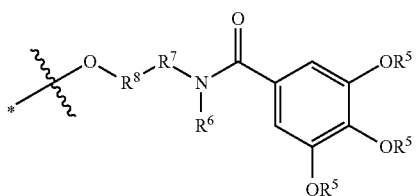

[wherein,
$R^5$ each independently represents an optionally substituted C6-C30 alkyl group, $R^6$ represents a group selected from an optionally substituted C1-C6 alkyl group, an optionally substituted C3-C6 cycloalkyl group, an optionally substituted non-aromatic heterocyclic group, an optionally substituted aryl group, an optionally substituted heteroaryl group, an optionally substituted aralkyl group, or an optionally substituted heteroaryl alkyl group, $R^7$ represents an optionally substituted C1-C6 alkylene group, or an optionally substituted C1-C6 alkyleneoxy group, $R^8$ represents an optionally substituted C1-C6 alkylene group, or alternatively, $R^6$ and $R^7$ combined together with a nitrogen atom to which they are attached may form an optionally substituted non-aromatic heterocyclic group or an optionally substituted heteroaryl group, or alternatively, $R^6$, $R^7$ and $R^8$ combined together with a nitrogen atom to which they are attached may form an optionally substituted non-aromatic heterocyclic group, an optionally substituted non-aromatic heterocyclic alkyl group, an optionally substituted heteroaryl group, or an optionally substituted heteroaryl alkyl group, and

* represents a binding position to L.].

(Nucleotide Compound)

Item [13] A nucleotide compound represented by formula (III):

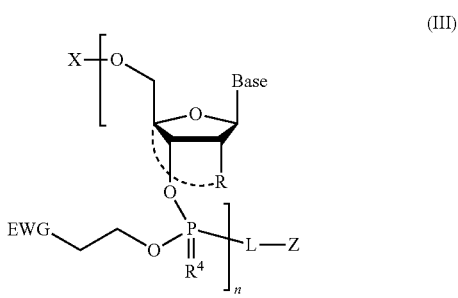

[wherein,
Z represents a pseudo solid phase protecting group represented by formula (II) as described in the Item [12], L represents a linker, Base each independently represents an optionally protected nucleic acid base, the number of n of EWG each independently represents an electrophilic group, the number of n of $R^4$ each independently represents an oxygen atom or a sulfur atom, the number of n of R each independently represents a hydrogen atom, a halogen atom, a hydroxy group optionally substituted with a protecting group, an optionally substituted C1-C6 alkoxy group, an organic group for bridging to 4'-carbon atom, or a bridge structural of artificial nucleic acid group, n is an arbitrary integer of 0 or more, and X represents a temporary protecting group which can be deprotected with an acid.].

Item [14] A nucleotide compound according to the Item [13] wherein L represents a formula represented by the following formula:

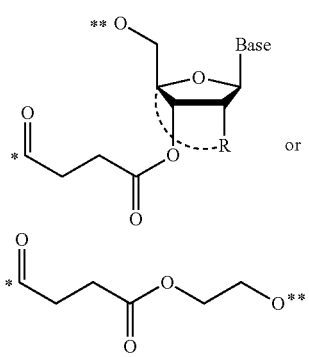

[wherein,
** represents a binding position to a hydrophobic group,
* represents a binding position to a phosphorus atom,
Base represents a nucleic acid base wherein each independently may be optionally protected; and
R each independently a hydrogen atom, a halogen atom, a hydroxy group optionally substituted with a protecting group, an optionally substituted C1-C6 alkoxy group, an organic group for bridging to 4'-carbon atom, or a bridge structural of artificial nucleic acid group].

Effect of Invention

According to the method for preparing and isolating the highly liposoluble phosphoramidite of the present invention, the highly liposoluble phosphoramidite can be isolated and prepared conveniently in high purity. Also the solution containing the highly liposoluble phosphoramidite obtained by the preparation method of the present invention, or the composition comprising the same solution and optionally an additive, can be used as a capping reaction reagent, and also a single elongation reaction of a nucleotide chain length can be effectively conducted by the above-mentioned preparation and purification method in combination with a worked-up treatment with a nucleotide reagent after the capping reaction.

BRIEF DESCRIPTION OF DRAWINGS

FIG. 1 is a figure showing a recovery yield of a phosphoramidite product (monoamidite compound) in the Examples 1 to 4.
FIG. 2 is a figure showing each NMR chart (excerpt parts of 6.0-9.5 ppm) of a mixture of the compound DMT-diacyl-dA-Su-R and the compound DMT-dA-Su-R (upper column) and the compound DMT-dA-Su-R (lower column).

MODE FOR CARRYING OUT THE INVENTION

Hereinafter, the present invention is further described in detail.
Unless otherwise specified in the sentences, any technical terms and scientific terms used herein, have the same meanings as those generally understood by those of ordinary skill in the art the present invention belongs to. Any methods and materials similar or equivalent to those described in herein can be used for practicing or testing the present invention, and preferable methods and materials are described as follows. All publications and patents referred to herein are hereby incorporated by reference so as to describe and disclose constructed products and methodology described in, for example, publications usable in relation to the described invention.

(Preparation and Purification Method of Highly Liposoluble Phosphoramidite)

According to one embodiment of the present invention, the present invention provides a method for preparing compound represented by formula (I):

[wherein,
$R^1$ represents an optionally substituted C6-C30 alkyloxy group, and the substituent is at least one group selected from a C1-C3 alkyl group or a C3-C6 cycloalkyl group,
$R^2$ each independently represents an optionally substituted C1-C6 alkyl group, and the substituent is at least one group selected from a C1-C3 alkyl group or a C3-C6 cycloalkyl group, and
$R^3$ represents an optionally substituted C6-C30 alkyloxy group, an optionally substituted C1-C8 alkyloxy group, or an optionally substituted C2-C8 alkynyloxy group, and the substituent in the optionally substituted C6-C30 alkyloxy group is at least one group selected from a C1-C3 alkyl group, or a C3-C6 cycloalkyl group, and the substituent in the optionally substituted C1-C8 alkyloxy group or the optionally substituted C2-C8 alkynyloxy group is a cyano group (CN).]

(hereinafter, referred to as "highly liposoluble phosphoramidite of the present invention"),
which comprises the following steps:
(1) reacting an aliphatic alcohol and a trivalent phosphorus compound in organic solvent in the presence of an activator or an organic base;
(2) washing the resulting reaction mixture with water in a separatory funnel;
(3) recovering the organic layer after the step (2) and concentrating it (with the proviso that the organic solvent used in the step (1) is a nitrile solvent, the steps (2) to (3) may be omitted);
(4) solubilizing the resulting residue obtained in the step (3) in an aliphatic hydrocarbon solvent (with the proviso that the organic solvent used in the step (1) is an aliphatic hydrocarbon solvent, the steps (2) to (3) may be omitted);
(5) washing the aliphatic hydrocarbon solution prepared in the step (4) with a nitrile solvent in a separatory funnel;
(6) recovering the aliphatic hydrocarbon solution after the step (5) to obtain a solution of a phosphoramidite compound (hereinafter, referred to as "Preparation method of highly liposoluble phosphoramidite of the present invention").

A phosphoramidite compound which is obtained by the preparation method of the present invention has a property of high affinity with organic solvent (for example, a hydrophobic solvent such as an aliphatic hydrocarbon solvent), while a low affinity with water, that is, a highly liposoluble property.

The term of "(an) optionally substituted C6-C30 alkyloxy group" used herein as $R^1$ and/or $R^3$ represents a hydrocarbon chain group having 6 to 30 carbon atoms which is attached to an oxygen atom, and a primary or the secondary alkyloxy group is preferably included, and these groups may be optionally substituted, and the example of the substituent is a group at least one selected from a C1-C6 alkyl group or a C3-C6 cycloalkyl group, and the alkyloxy group may optionally contain an aromatic ring, a cyano group, a group containing an ester bond, or a group containing an amide bond. The alkyl group may be a straight or branched group, and preferably a straight alkyl group. An example of the optionally substituted C6 to C30 alkyloxy group includes preferably a group showing more hydrophobic than a temporary protecting group X at 5'-position of a nucleic acid. Specific examples thereof includes preferably a C8 to C30 primary or secondary alkyloxy group, more preferably a C10-C30 primary or secondary alkyloxy group, and still more preferably C10 to C20 primary or secondary alkyloxy group. Specific preferred examples thereof includes a C18 primary or secondary alkyloxy group, and particularly a C18 primary alkyloxy group. With respect to a substituent, a kind of the substituent is not limited as long as they may not inhibit any reactions used in the present invention (for example, a capping reaction, and a coupling reaction, a deprotection reaction, a deblocking reaction, an oxidation reaction, a sulfidation reaction in a synthesis of oligonucleotide), and the substituent includes one or more groups selected from a C1-C6 alkyl group or a C3-C6 cycloalkyl group. Specific examples of the substituent include methyl, ethyl, isopropyl, cyclopropyl, and cyclohexyl.

Examples of "C1-C6 alkyl group" include methyl, ethyl, propyl, isopropyl, butyl, pentyl, and hexyl.

Examples of "C3-C6 cycloalkyl group" includes cyclopropyl, cyclobutyl, cyclopentyl, and cyclohexyl.

The term of "(a) group containing an ester bond" represents an alkylcarboxyl group, and for example, includes methylcarboxyl, ethylcarboxyl, and isoropylcarboxyl group. Here the group containing an ester bond is intended to encompass both an acyloxy type group and an alkoxycarbonyl type group.

The term of "(a) group containing an amide bond" represents an alkylamide group wherein an alkyl group may be optionally substituted with an alkyl group on a nitrogen atom. Examples thereof include an amide, a N,N-dimethylamide, and a N,N-diethyamide. Here the group containing an amide bond is intended to encompass an amide type group and a carboxamide type group.

According to one embodiment of the present invention, $R^1$ represents an optionally substituted C10-C30 primary or secondary alkyloxy group, and $R^3$ represents —OCH$_2$CH$_2$CN, —OCH$_3$, or —OCH$_2$CH$_3$, and preferably —OCH$_2$CH$_2$CN.

The term of "(an) optionally substituted C1-C6 alkyl group" used herein as $R^2$ represents a saturated hydrocarbon chain group having 1 to 6 carbon atoms. The alkyl group may be a straight or branched alkyl group. Examples of the optionally substituted C1-C6 alkyl group preferably include a C3 alkyl group. One specific example of preferred one thereof include an isopropyl.

With respect to a substituent, a kind of the substituent is not limited as long as they may not inhibit any reactions used in the present invention (for example, a capping reaction, and a coupling reaction, a deprotection reaction, a deblocking reaction, an oxidation reaction, a sulfidation reaction in a synthesis of oligonucleotide), and the substituent includes one or more groups selected from a C1-C3 alkyl group or a C3-C6 cycloalkyl group, and preferably C1-C3 alkyl group.

According to one embodiment of the present invention, each $R^2$ represents independently of each other an optionally substituted C1-C6 alkyl group, and preferably an optionally substituted C3-C6 alkyl group.

According to one embodiment of the present invention, each $R^2$ represents a i-propyl group.

The term of "(an) optionally substituted C1-C8 alkyloxy group" and "(an) optionally substituted C2-C8 alkynyloxy group" used herein as $R^3$ represents an alkyl group having 1 to 8 carbon atoms, or an alkynyl group having 1 to 8 carbon atoms which is attached to an oxygen atom, and may be optionally substituted with a cyano group. The alkyl group or the alkynyl group may be preferably the primary or secondary group thereof, and may be a straight or branched group, and preferably a straight group. Specifically, a C1-C6 alkoxy group or a C1-05 alkynyloxy group is preferably included, and a C1-C3 alkyloxy group is more preferably included.

Specific examples of the preferred $R^3$ group include —OCH$_2$CH$_2$CN, —OCH$_3$ or —OCH$_2$CH$_3$, and preferably —OCH$_2$CH$_2$CN.

According to one embodiment of the present invention, in the formula (1), $R^1$ represents an optionally substituted C10-C30 primary or secondary alkyloxy group, and $R^3$ includes —OCH$_2$CH$_2$CN, —OCH$_3$ or —OCH$_2$CH$_3$.

According to one embodiment of the present invention, specific examples of the compound represented by formula (I) includes the compounds represented by the following formulae.

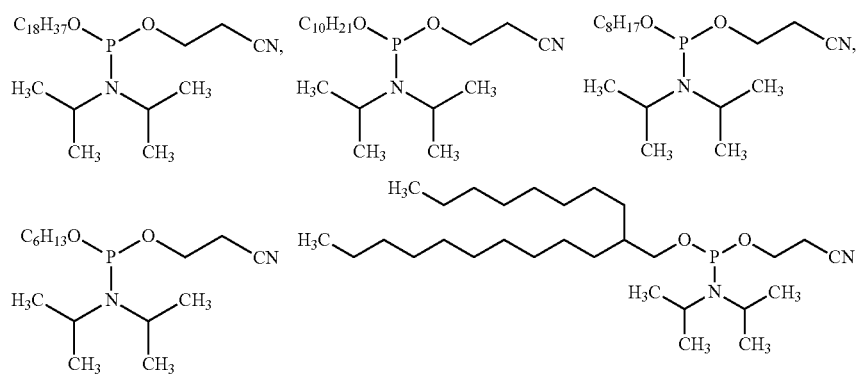

-continued

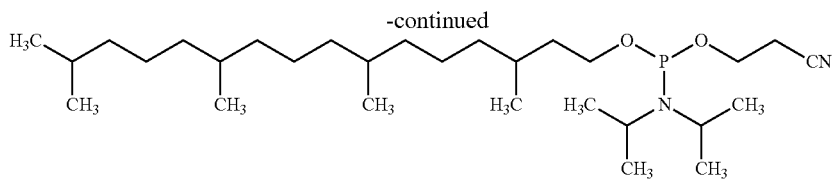

The compound represented by formula (I) of the present invention is so-called an amidite type compound (monoamidite compound), and can be used as a capping reagent in the preparation of an oligonucleotide of the present invention using a phosphoramidite method. Here the compound represented by formula (I) which is used in the present invention shows more highly liposoluble, that is, more high hydrophobic property than a phosphoramidite compound of nucleotide or oligonucleotide for a coupling reaction used in a phosphoramidite method, which is thus largely different from the desired oligonucleotide products or an unreacted raw materials that are remained in a coupling reaction in a physical property (for example, an affinity with silica gels and ODS modified silica gels), which can thus detect the desired oligonucleotide product distinguishably from the unreacted raw materials to which a capping reagent is attached.

Also, the compound represented by formula (I) as a capping reagent of the present invention is less sterically-hindered around a phosphoramidite moiety than any nucleotide phosphoramidite compound for coupling reaction, and thus shows very high reactivity, and has a high capping reactivity with an unreacted raw materials or oligonucleotide, which can achieve a desired coupling reaction in a small amount used of the compound of formula (I).

(Step 1)

The term of "an aliphatic alcohol" in the step (1) represents an aliphatic alcohol having 6 to 30 carbon atoms, preferably the primary or secondary hydrocarbon aliphatic alcohol, and specifically, corresponds to an aliphatic alcohol which contains an aromatic ring and also supplies an optionally substituted C6-C30 alkyloxy group, which is defined a $R^1$ group. Examples thereof include a long chain primary or secondary aliphatic alcohol having preferably as the number of carbon atoms C8 to C30, more preferably C10 to C30, and still more preferably C10 to C20. One example of the preferred one thereof include the primary or secondary C18 aliphatic alcohol, in particular, the C18 primary aliphatic alcohol.

The term of "trivalent phosphorus compound" in the step (1) represents, for example, alkylphosphoramidite, and alkylchlorophosphoramidite. Specific examples thereof include 2-cyanoethyl-N,N,N',N'-tetraisopropylphosphoramidite, and 2-cyanoethyl diisopropylchlorophosphoramidite.

Examples of the term of "activator" in the step (1) include tetrazole compounds. Specific examples thereof include 1H-tetrazole, and 5-ethylthio-1H-tetrazole (abbreviated as ETT), which are not limited thereto.

The term of "organic base" in the step (1) is used in the case where alkylchlorophosphoramidite is used as a trivalent phosphorus compound, and examples thereof include triethylamine and diisopropylethylamine.

Examples of the term of "organic solvent" in the step (1) include halogen solvents, nitrile solvents and cyclic ether solvents, and preferably halogen solvents. These organic solvents are preferably anhydrous organic solvents. Specific examples thereof include dichloromethane, chloroform, carbon tetrachloride, dioxane, and tetrahydrofuran and the others, which are not limited thereto. Dichloromethane and chloroform are preferably included.

The reaction temperature is usually within a range of −20 to 50° C. The reaction period is usually within a range of 0.1 to 10 hours. It is also recommended that the reaction is conducted under an inert gas.

The mixed molar ratio of the aliphatic alcohol to the trivalent phosphorous compound includes, for example, a range of 0.5 to 1.5 molar equivalents, and preferably excess amounts (for example, 1.1 molar equivalent amounts) of the trivalent phosphorus compound.

(Step 2)

In the step (2), the reaction mixture obtained in the step (1) are poured into a separatory funnel and the organic layer is washed with water (for example, a distilled water) in a separatory funnel. The amount of washing water is not limited otherwise specified, and may be a used amount of a volume ratio 0.1 to 5 v/v as opposed to the amount of the organic solvents used in the step (1).

(Step (3))

The organic layer after washing in the step (2) is recovered, and the organic solvents are distilled and concentrated, for example, with an evaporator under reduced pressure. Here when the organic solvents used in the above-mentioned step (1) is a nitrile solvent, the above-mentioned steps (2) to (3) may be omitted.

(Step (4))

An aliphatic hydrocarbon solvent is added to the residue obtained in the step (3) and the residue is solubilized. Specific examples of the aliphatic hydrocarbon solvent include pentane, hexane, heptane and octane and the others, which are not limited thereto. Pentane, hexane, and heptane are preferably included, and particularly preferably heptane. The addition amount of the aliphatic hydrocarbon solvent may be varied depending on the solubility of the highly liposoluble phosphoramidite compound in the reaction product against the aliphatic hydrocarbon solvent used, and may be an appropriate amount to solubilize, and includes about 1 to 500 times mL opposed to 1 mmol of the aliphatic alcohol used in the step (1) and typically about 1 to 10 times mL. Here when the organic solvent used in the above step (1) is an aliphatic hydrocarbon solvent, performing of the above-mentioned steps (2) to (4) may be omitted.

(Step 5)

The aliphatic hydrocarbon solution prepared in the step (4) is poured into a separatory funnel, and washed with a nitrile solvent. Specific examples of the nitrile solvent are not limited as long as the solvent can be phase-separated from the organic layer of the solution of the products contained in the aliphatic hydrocarbon solvent in a separatory funnel, and include, for example, hydrous acetonitrile, acetonitrile, propionitrile, and benzonitrile. Acetonitrile is particularly preferred. The amount of the nitrile solvent for washing is not limited otherwise specified, and may be a used amount of a volume ratio of 0.1 to 10 v/v as opposed to the amount of the organic solvents in the step (3), alternatively, may be a used amount of a volume ratio of 0.1 to 10 v/v as opposed to the amount of the aliphatic hydrocarbon solvent. The number of washing is not limited to once, and can be determined easily by confirming a presence of H-phosphonate compound and/or an amidite compound through a $^{31}P$ NMR measurement of a partial of the washed aliphatic hydrocarbon solution.

(Step 6)

The aliphatic hydrocarbon solution obtained after washing in a separatory funnel in the step 5 is recovered to obtain the desired phosphoramidite compound as a solution containing the same.

The obtained solution can be used in the next step (for example, a capping reaction step) by removing dissolved water. Alternatively, the obtained solution can be concentrated, for example, with an evaporator under reduced pressure as needed, to use in the next reaction step.

As aforementioned, in a preparation of the highly liposoluble phosphoramidite compound represented by formula (I) of the present invention, the purification of the desired product can be conducted by only a treatment in a separatory funnel, as worked-up treatment after the production reaction, and the desired product can be prepared conveniently. When the purification is conducted only by using a separatory funnel, a phosphorous acid triester compound, which is a tri-substituted alkyl compound of the compound (I), is contained in the obtained product in a small amount (for example, 0.1% or more), however, the phosphorous acid triester compound does not have any reactivity against oligonucleotide raw materials and their products. There is no problem in a used as a capping reagent even though they are contained in the compound represented by formula (I). Also with respect to a solution of the desired phosphoramidite compound (monoamidite compound) in an aliphatic hydrocarbon solvent which is obtained in the step (6), an oligonucleotide raw materials, H-phosphonate compound which may produce by-products (such as 2-cyanoethyl N,N-diisopropyl phosphonamidate) and the diamidite compound, a hydrocarbon aliphatic alcohol as a raw material (for example, see Example 6) can be removed from an aliphatic hydrocarbon solution by a washing procedure with water used in the step (2) and a nitrile solvent used in the step (4), and can be obtained as a solution containing the desired monoamidite compound having high purity being substantially pure.

(Solution for Capping Reaction and Capping Reaction)

According to one embodiment of the present invention, the present invention provides a capping method using a solution containing the highly liposoluble phosphoramidite compound which is prepared by the preparation method of the highly liposoluble phosphoramidite of the present invention, or optionally a composition to which an additive (such as a stabilizer) is added, as a capping reaction reagent (which is referred to as "capping reaction reagent of the present invention") (hereinafter, said method is referred to as "a capping reaction of the present invention").

The reaction scheme I is shown as a capping reaction below.

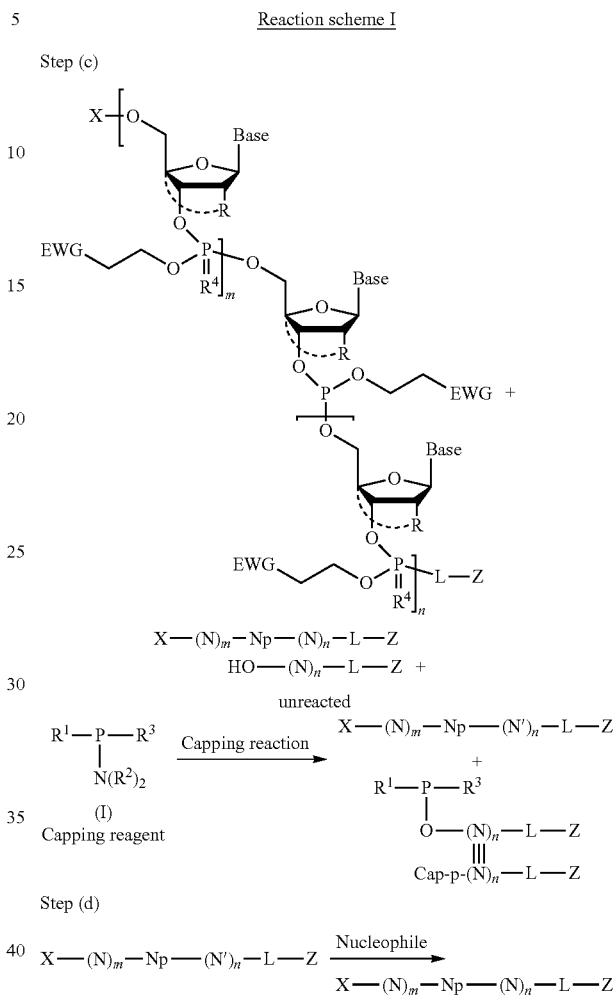

The term of "capping" used herein represents a protection of a group at the reaction active site in unreacted chain of a nucleoside, a nucleotide, or two or more compounds selected from oligonucleotide in an elongation reaction of a nucleotide chain, typically in a coupling reaction (such as a phosphoramidite method) between nucleotides. Capping reaction can prevent a proceeding of an elongation reaction at an reaction active site of the oligonucleotide chain which has been retained before the coupling reaction in competition with the reaction active site in the desired oligonucleotide chain in the next coupling reaction, and thus can prevent a side-production of a N–1 oligonucleotide.

According to one embodiment of the present invention, the present invention provides a capping method which comprises a step of contacting the reaction solution after the coupling reaction of two or more compounds selected from nucleoside, nucleotide, or oligonucleotide with the capping reaction reagent of the present invention (that is, a solution containing a highly liposoluble phosphoramidite compound which is obtained by the preparation method of highly liposoluble phosphoramidite of the present invention, or a composition containing the same solution and optionally an additive) optionally in the presence of an activator (step (c) in the above reaction scheme I)
(hereinafter, referred to as "Capping method of the present invention").

According to one embodiment of the present invention, the capping method of the present invention may comprise, as needed, further a step of reacting a capping side-product with a nucleophile after the capping reaction step (the same step (d)). Here the step (d) may optionally comprise a step of adding an organic base after the capping reaction step, followed by reacting with a nucleophile. Here examples of the organic base include 2,4,6-collidine, 2-picoline, 2,6-lutidine, 1-methylimidazole, and pyridine, which are not limited thereto.

The term of "nucleotide" as used herein represents an nucleic acid component including sugar moiety (such as ribose sugar), derivatives of the sugar moiety, a base or a basic group which is covalently bonded to those having equivalent functionality to those of the sugar moiety (such as analogues of carbocycle and the like) (such as at least one of homocycle, at least one of heterocycle, at least one of aryl group). For example, when the nucleoside contains a sugar moiety, the base is typically bounded at a 1'-position of the sugar moiety. Examples of the base include the followings.

The term of "nucleotide" as used herein represents an ester of nucleoside, for example, phosphate ester of a nucleoside.

The term of "oligonucleotide" as used herein represents a nucleic acid comprising at least two nucleotides, typically three or more (such as four) nucleotides, more typically more than 10 nucleotides which is capable of forming a double strand due to a complementary strands at room temperature. The total number of nucleotide indicates "n" in the present invention. Examples of the oligonucleotide include a single strand nucleotide, or chemically modified substances, including a nucleotide having 2'-O, 4'-C-methylene bridge on these sugar moieties (such as bridged structural type of artificial nucleic acid (BNA: Bridged Nucleic Acid) and the others). Examples of the BNA include locked artificial nucleic acid (LNA: Locked Nucleic Acid), 2'-, 4'-C-ethylene bridged type nucleic acid (ENA: 2'-O, 4'-C-Etylenebridged Nucleic Acid). Hereinafter, specific structures (nucleoside moiety) of BNA including LNA and ENA which can be used in the present invention are shown by referring to Drawings described in WO 2016/006697.

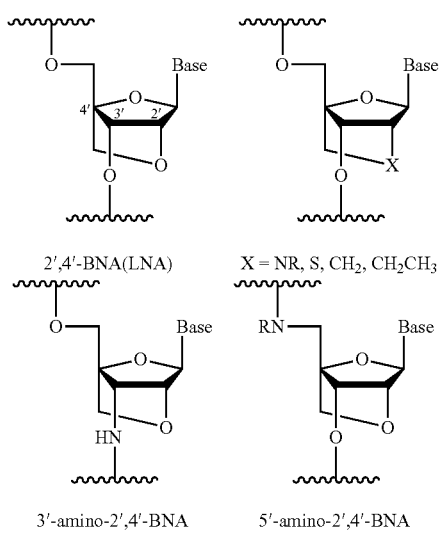

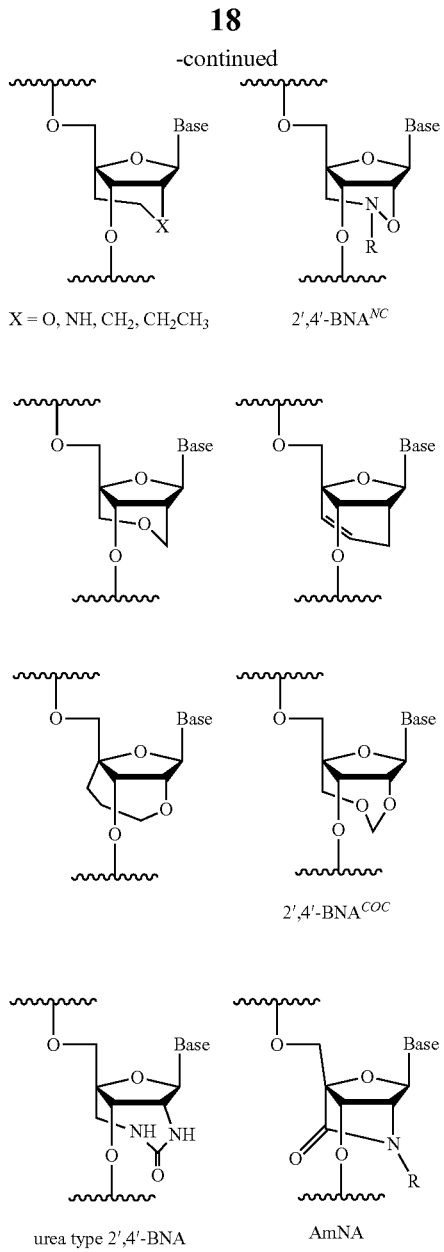

Examples of the modified substances includes any modified backbones of the oligonucleotide, which is not limited thereto, and include typically modified substances which is described in Micklefield (2001) "Current Medicinal Chemistry" 8: 1157-1170, for example, peptide nucleic acid (PNA), phosphorothioate DNA, methylphosphonate DNA and the like. The oligonucleotide consists of any combination of the above-mentioned nucleotides and the above-mentioned modified substances.

The term of "Base" as used herein each independently represents a group selected from an adenine residue, a guanine residue, a cytosine residue, a thymine residue, or an uracil residue, wherein these residues may be optionally substituted with a protecting group as needed.

In preferred specific embodiments of the present invention, examples of the nucleic acid base residue include a group represented by the following formulae.

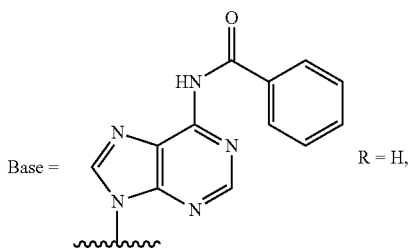

Base = A, R = H,

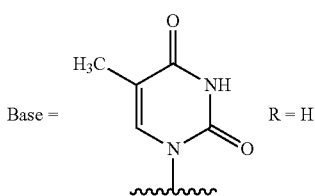

Base = T, R = H

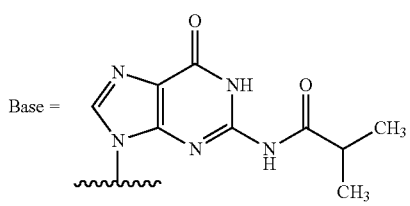

Base = G

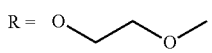

R =

(Step (c))

In the step (c), the below-mentioned step is included, in which a reaction solution obtained after the coupling reaction of two or more compounds selected from nucleoside, nucleotide, or oligonucleotide is contacted to the solution comprising the highly liposoluble phosphoramidite compound which is obtained by the method for preparing the highly liposoluble phosphoramidite of the present invention, or the composition comprising the same solution and optionally an additive, in the presence of an activator.

Examples of the two or more compounds selected from nucleoside, nucleotide, or oligonucleotide which is used in the coupling reaction of the step (c) include a combination in which one compound is a n-polymerized nucleoside, nucleotide or oligonucleotide which is obtained after a deblocking reaction following the step (a) in the reaction scheme I, which is represented by a formula: HO—(N)n-L-Z (wherein n is an arbitrary integer of 1 or more) wherein a 5'-hydroxy group is deblocked and at least one group of a 3'-hydroxy group or a nucleic acid base is substituted with a pseudo solid phase protecting group, and another compound is a m+1-polymerized oligonucleotide represented by a formula: X—(N)$_m$—Np (wherein m is an arbitrary integer of 0 or 1) wherein a 5'-hydroxy group is protected with a temporary protecting group which is removable under an acidic condition and a 3'-hydroxy group is phosphoramidited.

The reaction temperature of the capping reaction in the step (c) is usually within a range of −20 to 80° C. The reaction period in the reaction is usually within a range of 0 to 30 hours. Also the reaction is preferably conducted under inert gas atmosphere.

An amount used of the highly liposoluble phosphoramidite compound of the present invention as a capping reagent is, for example, within a range of usually 0.1 to 1.5 molar equivalents, preferably 0.1 to 0.5 molar equivalents as a mixing molar ratio as opposed to 1 mole amount of the n-polymerized nucleoside, nucleotide, or oligonucleotide for a coupling reaction represented by the above-mentioned formula: HO—(N)$_n$-L-Z.

Examples of the activator that may be used in the step (c) include any reagents which is generally known to be usable in a capping reaction using a phosphoramidite method, specifically tetrazoles (such as 1H-tetrazole, 5-ethylthio-1H-tetrazole (abbreviated as ETT). The amount used of the activator is, for example, within a range of usually 1.0 to 10.0 molar equivalent(s), preferably 1.0 to 2.0 molar equivalent(s) as a mixing molar ratio as opposed to 1 mole amount of the highly liposoluble phosphoramidite compound of the present invention as a capping reagent, and an extra corresponding equivalent thereof may be added in advance in the step (b).

(Step (d))

The capping method of the present invention may further comprise a step of reacting a by-product for a capping reaction with a nucleophile as needed, following the capping reaction step in the step (c). Examples of the nucleophile include any compounds selected from alcohol, phenol, carboxylic acid or N-alkylhydroxylamine, and specifically include ethanol, methanol or N-hydroxysuccinimide, preferably ethanol. The amount used of the nucleophile is, for example, within a range of usually 0.1 to 100 molar equivalents, preferably 1 to 20 molar equivalent(s) as a mixing molar ratio as opposed to 1 mole amount of the highly liposoluble phosphoramidite compound of the present invention as a capping reagent.

(Preparation Method of Oligonucleotide)

According to one embodiment of the present invention, the present invention provides a preparation method of oligonucleotide comprising the capping step of the present invention. The representative reaction scheme for preparation method of oligonucleotide of the present invention is shown in a Reaction Scheme II below.

Reaction scheme II
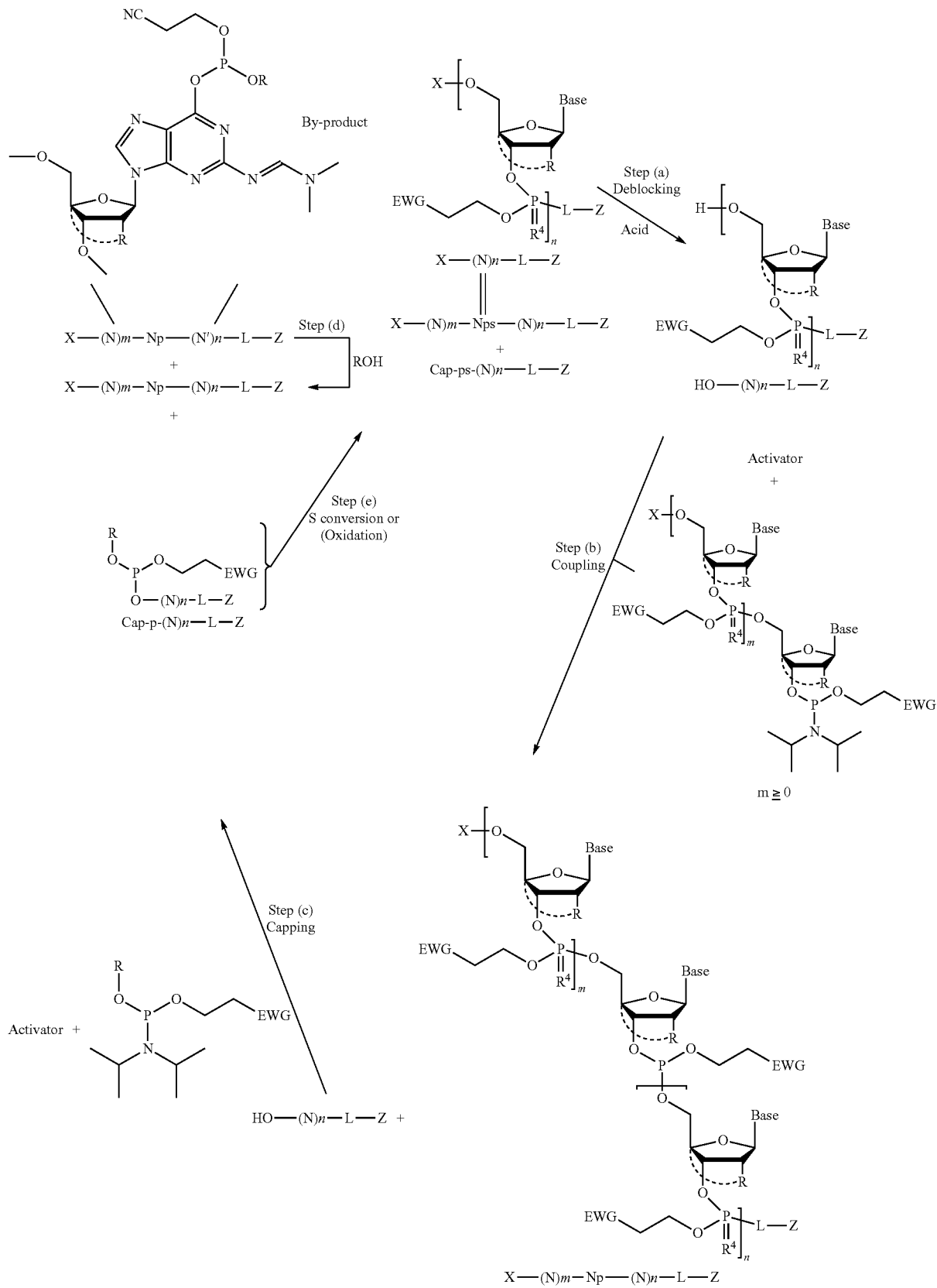

A preparation method of oligonucleotide of the present invention (hereinafter, referred to as "Preparation method of the present invention" or "Present preparation method") is explained in line with the above-mentioned descriptions of the reaction scheme II, which may be any commonly-known preparation methods for oligonucleotide, which is not be limited to the reaction scheme II.

Specifically, the preparation method of an optionally protected n+1+m-polymerized oligonucleotide (that is, n+1+m-mer) from an optionally protected n-polymerized oligonucleotide (that is, n-mer). Here when n is 1, the n-mer of oligonucleotide may encompass "nucleoside", and when m is 0, the m+1-mer of oligonucleotide may encompass "nucleoside".

The preparation method of oligonucleotide of the present invention comprises the following steps (a) to (e).
(Step (a): Deblocking Step and Reprecipitation Step)
The reaction scheme 1 of the step (a) is described below.

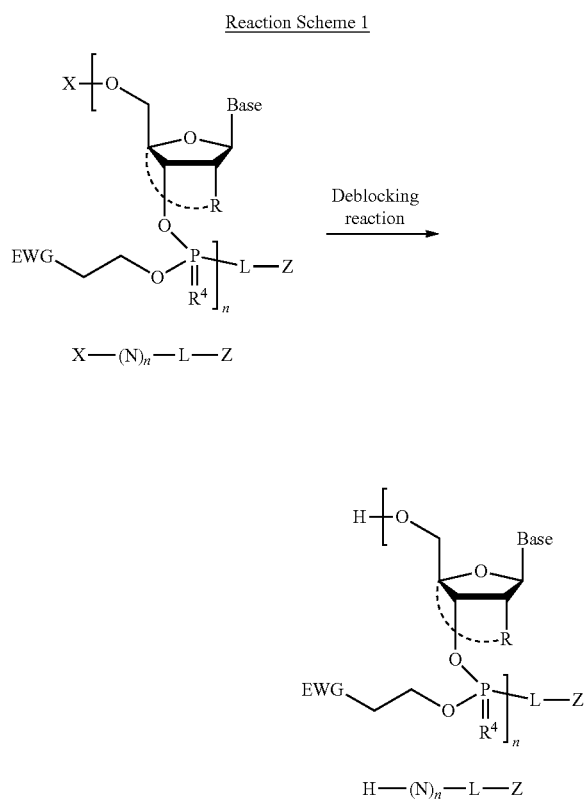

Reaction Scheme 1

In the step (a), it comprises the following steps:
a step in which a n-mer products (wherein n is an arbitrary integer of 1 or more) which is removable under an acidic condition wherein a 3'-hydroxy group or a nucleic acid base is modified with a pseudo solid phase protecting group, and also a 5'-hydroxy group is blocked with a temporary protecting group which is removable under an acidic condition, or when n is 0, a compound wherein one hydroxy group of a linker containing two or more hydroxy groups is modified with a pseudo solid phase protecting group, and another hydroxy group is blocked with a temporary protecting group which is removable under an acidic condition, for example, a compound represented by the above-mentioned formula: X—$(N)_n$-L-Z is reacted in a nonpolar solvent in the presence of an acid alone or in co-existence of a cation scavenger to deblock a protecting group for the hydroxy group (Deblocking Step), followed by a step in which a compound containing a pseudo solid phase protecting groups, for example, a compound represented by the above-mentioned H—$(N)_n$-L-Z using a polar solvent is recovered (reprecipitation step).

The deblocking step reaction may be conducted under a reaction condition described in the literature (for example, WO 2012/157723 A1). Specific explanations are described below.

The term of "pseudo solid phase protecting group" used herein may comprise any groups described in the literature (for example, WO 2012/157723 A1). Examples thereof include any pseudo solid phase protecting groups as below-mentioned herein, which is not limited thereto.

The temporary protecting group which is removable under an acidic condition for a 5'-hydroxy group is not particularly limited, as long as it is any groups which can be deprotected under an acidic condition and can be used a protecting group for a hydroxy group, and examples thereof may include trityl group, 9-(9-phenyl)xanthenyl group, 9-phenylxanthenyl group, 1,1-bis(4-methoxyphenyl)-1-phenylmethyl group (abbreviated as dimethoxytrityl group), 1-(4-methoxyphenyl)-1,1-diphenylmethyl group (abbreviated as monomethoxytrityl group) and the others. Dimethoxytrityl group and monomethoxytrityl group are preferably included.

The reaction solvent to be used in the deblocking step may be any solvents that do not affect the deblocking reaction, and examples thereof include preferably a solvent having high solubility for the (oligo)nucleotide compound as a reactant, and for example, a nonpolar solvent is preferred. Specific examples of the nonpolar solvent include halogen solvents, aromatic solvents, ester solvents, aliphatic solvents, nonpolar ether solvents, and any combinations selected from these solvents. Specific examples thereof include dichloromethane, chloroform, 1,2-dichloroethane, benzene, toluene, xylene, mesitylene, hexane, pentane, heptane, nonane, cyclohexane, ethyl acetate, isopropyl acetate, tert-butyl methyl ether, cyclopentyl methyl ether, and any combinations selected from these solvents.

The concentration of the n-mer oligonucleotide in solvents in this deblocking step is not particularly limited, as long as it is solubilized, and is preferably 1 to 30 weight %.

Specific examples of acid that can be used in this blocking step is not particularly limited, and include, for example, trifluoroacetic acid, trichloroacetic acid, trifluoromethanesulfonic acid, trichloroacetic acid, methanesulfonic acid, hydrochloric acid, acetic acid, p-toluenesulfonic acid and the others. Trifluoroacetic acid, dichloroacetic acid, and trichloroacetic acid are preferred.

The amount used of the acid may be within a range of 1 to 100 mole(s) as opposed to 1 mole of n-mer (oligo) nucleotide, and is preferably 1 to 40 mole(s).

The acid may be used singly, or may be used in co-existence of the cation scavenger. Examples of the cation scavenger is not particularly limited, as long as a re-protection by the removed protecting group X or a side reaction against a deprotected functional group does not proceed, and include pyrrole derivatives (such as pyrrole), and indole derivatives (such as indole), and furan derivatives. The amount used of the cation scavenger may be within a range of 1 to 50 mole(s) as opposed to 1 mole of the n-mer oligonucleotide, and is preferably 5 to 20 moles.

The reaction temperature of the deblocking step is not particularly limited, as long as the reaction can proceed, and, for example, is preferably −10 to 50° C., and more preferably 0 to 40° C. The reaction period in the reaction may be varied depending on a reaction condition, for example, the kind of n-mer (oligo)nucleotide as a reactant, the kind of the acid, the kind of the solvent, or the reaction temperature, and for example, may be within a range of 5 minutes to 5 hours.

In the step (a), the step may comprise a step in which following the deblocking step, the compound containing the pseudo solid phase protecting group after a neutralization reaction or as itself is precipitated out using a polar solvent to recover the compound.

Examples of the polar solvents include alcohol solvents and nitrile solvents, and specific examples thereof include methanol and acetonitrile.

(Step (b): Coupling Step)

The reaction scheme 2 of the step (b) is shown below.

Reaction scheme 2

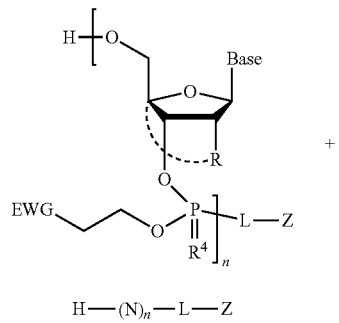

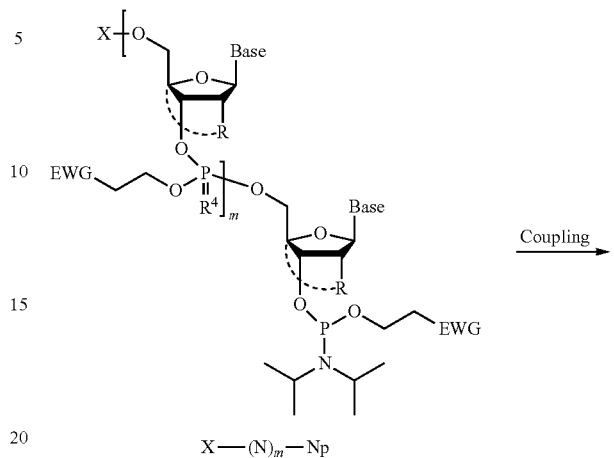

-continued

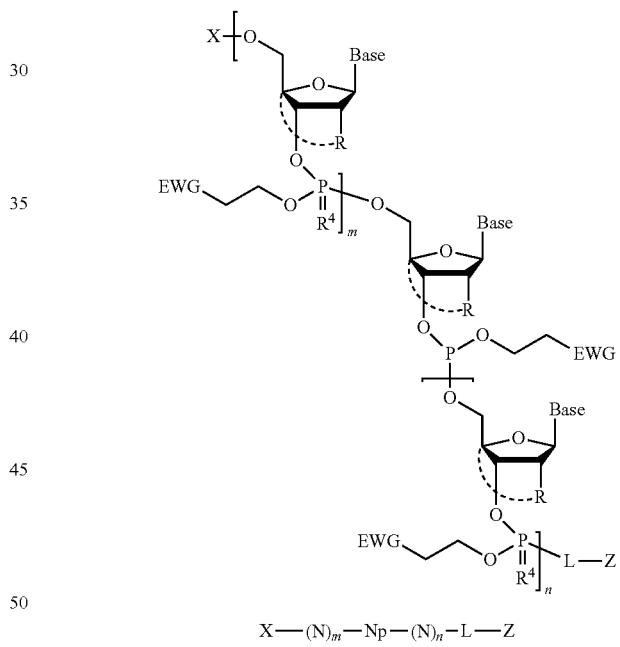

The coupling step reaction in the step (b) can be conducted under the reaction condition which is described in the literature (for example, WO 2012/157723 A1). Specific explanations thereof is described below.

In the step (b), after drying the recovered substances in the step (a), to the resulting residue in a non-polar solvent were added a m+1-polymerized (oligo)nucleotide wherein a 3'-hydroxy group is phosphoramidited and also a 5'-hydroxy group is protected with a temporary protecting group which is removable under an acid condition (wherein m is an arbitrary integer of 0 or more) and an activator to condense the m+1-polymerized (oligo)nucleotide to the n-polymerized (oligo)nucleotide obtained in the step (a) wherein a protecting group of the 5'-hydroxy group is deblocked by a phosphite triester bond through its 5' hydroxy group of the n-polymerized (oligo)nucleotide (Coupling step).

The upper limit value of m is not particularly limited, and for example, is preferably 49 or less, more preferably 29 or less, further preferably 19 or less, further more preferably 4 or less, and particularly preferably 2 or less (such 0).

The term of "m+1-polymerized (oligo)nucleotide wherein a 3'-hydroxy group is phosphoramidited, and a 5'-hydroxy group is protected with a temporary protecting group which is removable under an acidic condition" represents an (oligo)nucleotide to be coupled to the n-mer polymerized (oligo)nucleotide obtained in the step (a) wherein the protecting group for 5'-hydroxy group is deblocked (such as the compound represented by formula X—$(N)_n$-L-Z)).

In this coupling step, a weak acid or an acidic neutralized salt can be also added as an activator to increase a reaction efficiency. Examples of the weak acid or the acidic neutralized salt include pyridine, trifluoroacetate, 1H-tetrazole, 5-benzylthio-1H-tetrazole, 4,5-dicyanoimidazole, and the others.

The amount used of the weak acid or the acidic neutralized salt may be within a range of 0.1 to 50 molar equivalents as opposed to 1 mole of the n-polymerized (oligo)nucleotide obtained in the step (a) as a reactant wherein the protecting group for 5'-hydroxy group is deblocked, and is, for example, 1 to 5 molar equivalents.

Also, in this coupling step, since an acidity of the reaction solution becomes higher, a risk of developing a side reaction in which a temporary protecting group X is eliminated is happened, N-methyl imidazole is preferably added thereto to suppress an acidification of a reaction solution.

The amount used of the N-methyl imidazole may be within a range of 0.1 to 10 molar equivalents as opposed to 1 mole of n-polymerized (oligo)nucleotide obtained in the step (a) wherein the protecting group for 5'-hydroxy group is deblocked, and is, for example, within a range of 0.1 to 1 molar equivalents.

A compound ratio of "m+1-polymerized (oligo)nucleotide wherein a 3'-hydroxy group is phosphoramidited and also a 5'-hydroxy group is protected with a temporary protecting group which is removable under an acidic condition" to "n polymerized (oligo)nucleotide obtained in the step (a) wherein a protecting group for 5'-hydroxy group is deblocked" may be within a range of 1 to 10 mole(s) of the m+1-polymerized (oligo)nucleotide wherein the 3'-hydroxy group is phosphoramidited and also the 5'-hydroxy group is protected with a temporary protecting group which is removable under an acidic condition, as opposed to 1 mole of the n-polymerized (oligo)nucleotide obtained in the step (a) wherein the protecting group for 5'-hydroxy group is deblocked, and is preferably within a range of 1 to 5 molar equivalent(s).

This step is conducted in a solvent that does not affect a coupling reaction. Specific examples thereof include a nonpolar solvent as described in the above-mentioned step (a). Also nitrile solvents (such as acetonitrile), ketone solvents (such as acetone), amide solvents (such as N,N-dimethyl acetamide), polar ether solvents (such as 1,4-dioxane), and sulfoxide solvents (such as dimethyl sulfoxide) may be mixed with the above-mentioned nonpolar solvent by an appropriate ratio thereof, as long as the n-mer (oligo)nucleotide wherein the temporary protecting group of the 5'-hydroxy group is removed can be solubilized.

The reaction temperature of the step (b) is not particularly limited, as long as the reaction can proceed, and, for example, is within a range of preferably −20 to 100° C., and more preferably 20 to 50° C. The reaction period in the reaction may be varied depending on the kinds of the n-mer (oligo)nucleotide to be condensed and the reaction temperature and the like, and, for example, is within a range of 5 minutes to 24 minutes.

(Step (c) and Step (d))

According to one embodiment of the present invention, a step of conducting a capping reaction is provided, which comprises contacting a raw material that was unreacted in the step (b) to the highly liposoluble phosphoramidite compound which is obtained by a preparation method of the highly liposoluble phosphoramidite compound of the present invention.

Also according to one embodiment of the present invention, a step for a worked-up treatment may be included, in which following the capping reaction in the step (c), the by-product for the capping reaction is reacted with a nucleophile.

The details of the step (c) and the step (d) are as explained in the above-mentioned capping reaction of the present invention.

Here for the unreacted raw materials in the step (c), a n-mer (oligo)nucleotide obtained in the step (a) wherein a 5'-hydroxy group is deblocked (such as the compound represented by HO—$(N)n$-L-Z as shown in Reaction scheme 1) is included.

Also, for a by-product for capping reaction of the step (c) in the step (d), though no specific examples thereof has not been reported, a reaction product as an adduct with the capping reagent on the Base (such as alkoxylated phosphite triester product on a 6-oxygen atom in guanine) may be included. Also, in the case of the reaction products as an adduct with the capping reagent on the backbone of the Base (such as alkoxylated phosphite triester product on a 6-oxygen atom in guanine), it is expected that a reaction with a nucleophile can reproduce a guanine wherein an adduct molecule with a capping reagent is removed.

Here the reaction with a nucleophile in the present invention represents a reaction which is intended to be a treatment of a by-product of side reaction in a capping reaction. Accordingly, the reaction as described herein does not intend to the reaction in which a reaction solution following a coupling reaction step is quenched as described in the literature (for example, WO 2017/104836 A1).

(Step (e): Oxidation Reaction and Sulfidation Reaction)
Reaction scheme 3 of the step (e) is described below.

Reaction scheme 3

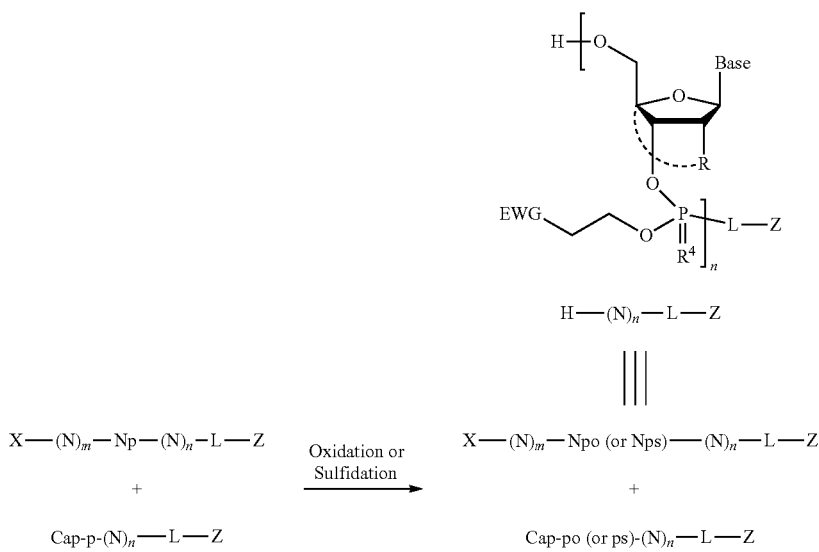

The oxidation reaction or sulfidation reaction in the step (e) can be conducted under a reaction condition as described in the literature (for example, WO 2012/157723 A1). Specific examples thereof is explained below.

In the step (e),
the following step is provided, in which an oxidizing agent or a sulfidizing agent is added to the reaction solution of the step (d) to convert a phosphite triester bond of the m+1+n-mer of oligonucleotide obtained in the step (d) to convert to a phosphate triester bond or a thiophosphate triester bond respectively (an oxidation step or a sulfidation step).

In this step, a reaction can be also conducted by adding an oxidizing agent or a sulfidizing agent directly to the reaction solution following the above-mentioned step (d), without isolating the m+1+n-mer of oligonucleotide obtained in the above-mentioned step (d).

The oxidation reaction with an oxidizing agent in the step (e) can be conducted according to the method which is usually known in an oligonucleotide synthesis. Examples of the oxidizing agent is not particularly limited, and include iodine, (1S)-(+)-(10-camphorsulfonyl)oxazolidine, tert-butyl hydroperoxide (TBHP), 2-butanone peroxide, 1,1-dihydroperoxycyclododecane, bis(trimethylsilyl)peroxide, and m-chloro perbenzoic acid, and preferably include iodine, (1S)-(+)-(10-camphorsulfonyl)oxazolidine, tert-butyl hydroperoxide (TBHP), 2-butanone peroxide, and 1,1-dihydroperoxycyclododecane.

The sulfidation reaction using a sulfidizing agent in the step (e) can be usually conducted according to a method which is usually known in an oligonucleotide synthesis. Examples of the sulfidizing agent is not particularly limited, and include, for example, 3-((N,N-dimethylaminmethylidene)amino)-3H-1,2,4-dithiazole-5-thione (DDTT), 3H-1,2-benzotiazole-3-one-1,1-dioxide (Beaucage reagent), 3H-1,2-benzothiazol-3-one, phenylacetyl-disulfide (PADS), tetraethyl lithium disulfide (TEAD), 3-amino-1,2,4-dithiazol-5-thione (ADTT), and sulfur, and 3-((N,N-dimethylaminomethylidene)amino)-3H-1,2,4-dithiazole-5-thione and 3H-benzothiazole-3-one-1,1-dioxide are preferably included.

The sulfidation reaction of a phosphite triester bond in the oligonucleotide converts to a thiophosphate triester bond. The thiophosphate contains an asymmetric center on a phosphorus atom, which thus provide an optically active product. Also, even if a deprotection reaction is conducted in the preparation step of oligonucleotide thiophosphate, the asymmetric center on a phosphorus atom is remained, which thus provide an optically active product. Accordingly, since an asymmetric center is present on each phosphorus atom in the constitute nucleotide, an oligonucleotide thiophosphate product becomes a mixture of a plural of optically active isomers, which results in a difficulty in a purification of the desired product, and it is thus required for a synthesis method providing a higher purity.

The reaction is usually conducted in a solvent. Examples of the solvents to be used in the reaction include preferably an anhydrous solvent, and examples thereof include halogen solvents (such as chloroform), aliphatic solvents (such as cyclohexane), aromatic solvents (such as toluene), ester solvents (such as ethyl acetate), ether solvents (such as tert-butyl methyl ether), nitrile solvents (such as acetonitrile), and mixed solvents of the solvents selected from two or more of these solvents.

An amount used of the oxidizing agent or the sulfidizing agent is within a range of about 1.0 to about 5.0 mole(s), preferably about 1.0 to about 1.5 mole(s), as opposed to 1 mole of the phosphoramidite obtained in the step (d).

The reaction temperature is usually within a range of 0 to 50° C. The reaction period in the reaction is usually within a range of 0.2 to 1 hour(s).

The amount used of the oxidizing agent or the sulfidizing agent may be within a range of 1 to 50 molar equivalent(s), preferably 1 to 5 molar equivalent(s), as opposed to 1 mole of the (oligo)nucleotide obtained in the step (d).

The reaction temperature is not particularly limited, and, for example, is within a range of 0 to 100° C., and preferably 20 to 50° C. The reaction period in the reaction may be varied depending on the kinds of the n+1+m-mer of the oligonucleotide, each of the kinds of the oxidizing agent or the sulfidizing agent used, and the reaction temperature, and include, for example, within a range of 1 minutes to 3 hours.

(Step f: Steps of Precipitation Out and Solid-Liquid Separation)

The procedures for precipitation out and solid-liquid separation can be conducted under the reaction condition which is described in the literature (for example, WO 2012/157723 A1). Specific explanations are described below.

According to one embodiment of the present invention, a preparation method of oligonucleotide of the present invention further may comprise a step in which a polar solvent is added to the reaction solution obtained in the step (e) to precipitate out the m+1+n-mer of oligonucleotide and then obtain it by a solid-liquid separation (that is, Step of Precipitation out and Solid-liquid separation).

The preparation method of the oligonucleotide of the present invention is required for a purification step that consists of a precipitation out and a solid-liquid separation of the m+1+n-mer oligonucleotide products to use a pseudo solid phase protecting group and obtain the m+1+n-mer oligonucleotide.

Examples of the polar solvents include alcohol solvents (such as methanol, and ethanol), nitrile solvents (such as acetonitrile), ketone solvents (such as acetone), ether solvents (such as tetrahydrofuran), amide solvents (such as dimethylformamide), sulfoxide solvents (such as dimethyl sulfoxide), water, and mixed solvents of two or more of these solvents. The alcohol solvents or the nitrile solvents is preferably included, and methanol is more specifically included.

Also the polar solvents may contain water so as to minimize a loss of the products into a polar solvent. The contents of water as opposed to the polar solvent is, for example, within a range of 0 to 10% (v/v), and preferably 0 to 8% (v/v).

Also, in the step (e), following a completion of the oxidation reaction or the sulfidation reaction, the resulting residue is reacted with a trivalent phosphorus reagent (such as triethyl phosphite) to remove an excess of the oxidizing agent or the sulfidizing agent, and then the solvents for precipitating out is added, or alternatively, in the precipitation out (such as a solution in which a solvent for precipitation out is saturated with sodium thiosulfate (hypo)) may be used. The amount of the sodium thiosulfate (hypo) installed depends on the amounts used of the solvents for precipitation out and the reaction temperature, and the reaction with trivalent phosphorus reagent is more preferably included.

(Step g: Deprotection Step)

The procedures for precipitation out and solid-liquid separation procedures in the step (f) can be conducted under the reaction condition which is described in the literature (for example, WO 2012/157723 A1). Specific explanations are described below.

According to one embodiment of the present invention, in the preparation method for oligonucleotide of the present invention, further, as needed, following each of the steps, a deprotection reaction of each protecting group is conducted depending on the kinds of the protecting group and properties, to isolate and obtain the oligonucleotide.

According to one embodiment of the present invention, the preparation method of the oligonucleotide of the present invention may further comprise as needed, a step (g): a step of removing all protecting groups of the m+1+n-polymerized oligonucleotide obtained in the step (f).

Example of the deprotection method includes a step in which all protecting groups of the oligonucleotide are removed according to the deprotection method which is described in, for example, Protective Group In Organic Synthesis, third edition, John Willy & Sons published (1999).

(Confirmation of Progress of Reaction)

The progress of a reaction of each step in the above-mentioned preparation method of oligonucleotide can be monitored and confirmed according to the similar method to that of a general liquid phase organic synthesis reaction. For example, the monitoring and confirming can be conducted by a thin layer silica gel chromatography (TLC) and high performance liquid chromatography (HPLC) and the others.

(Pseudo Solid Phase Protecting Group and Nucleotide Compound Containing the Same Group)

According to one embodiment of the present invention, the preparation method of oligonucleotide of the present invention can be conducted according to a liquid phase method using a nucleotide containing a pseudo solid phase protecting group.

The term of "Pseudo solid phase protecting group" represents a protecting group having both a reactivity and a simplicity for worked-up treatment in which the same group binds to a reaction substance to solubilize in a nonpolar solvent, which makes it possible to conduct a reaction in a liquid phase, and an addition of a polar solvent can precipitate out a product containing the pseudo solid phase protecting group, which makes it possible to conduct a solid-liquid separation, and it may be not particularly limited as long as it may be a group which is stable under an acidic condition removable a protecting group of 5'-terminal hydroxy group. Examples of the pseudo solid phase protecting group include any groups disclosed in the literature (for example, WO 2012/157723 A1), and preferred examples of the pseudo solid phase protecting group which is used in the preparation method of oligonucleotide of the present invention include a N-alkyl represented by the following formula (II) and a residue of an alkyl alcohol compound.

According to one embodiment of the present invention, the present invention provides a pseudo solid phase protecting group represented by formula (II):

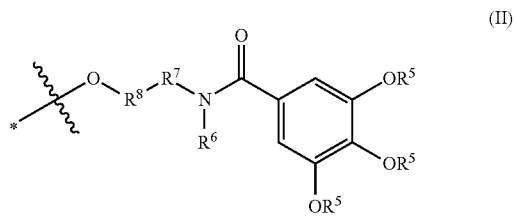

[wherein
$R^5$ each independently represents an optionally substituted C6-C30 alkyl group,
$R^6$ represents a group selected from an optionally substituted C1-C6 alkyl group, an optionally substituted C3-C6 cycloalkyl group, an optionally substituted non-aromatic heterocyclic group, an optionally substituted aryl group, an optionally substituted heteroaryl group, an optionally substituted aralkyl group, or an optionally substituted heteroaryl alkyl group, $R^7$ represents an optionally substituted C1-C6 alkylene group or an optionally substituted C1-C6 alkyleneoxy group, $R^8$ represents an optionally substituted C1-C6 alkylene group, or $R^6$ and $R^7$ combined with a nitrogen atom to which $R^6$ is attached may form an optionally substituted non-aromatic heterocyclic group, or an optionally substituted heteroaryl group, or $R^6$, $R^7$ and $R^8$ combined together with a nitrogen atom to which $R^6$ is attached may form an optionally substituted non-aromatic heterocyclic group, an optionally substituted non-aromatic heterocyclic alkyl group, an optionally substituted heteroaryl group, or an optionally substituted heteroaryl alkyl group, and

* presents a binding position to L.

According to one embodiment of the present invention, preferred example of a pseudo solid phase protecting group include a pseudo solid phase protecting group represented by formula (II)

wherein $R^5$ each independently represents an optionally substituted C8-C24 alkyl group, $R^6$ represents a group selected from an optionally substituted C1-C3 alkyl group, an optionally substituted C5-C6 cycloalkyl group, an optionally substituted aryl group, an optionally substituted heteroaryl group, or an optionally substituted aralkyl group, $R^7$ represents an optionally substituted C1-C4 alkylene group, $R^8$ represents an optionally substituted C1-C2 alkylene group, or $R^6$ and $R^7$ combined together with a nitrogen atom to which $R^6$ is attached may form an optionally substituted non-aromatic heterocyclic group, or an optionally substituted heteroaryl group, or $R^6$, $R^7$ and $R^8$ combined together with a nitrogen atom to which $R^6$ is attached may form an optionally substituted non-aromatic heterocyclic group, or an optionally substituted non-aromatic heterocyclic alkyl group.

The term of "(an) optionally substituted C6-C30 alkyl group" for $R^5$ as used herein represents a primary or secondary saturated hydrocarbon chain group containing a C6 to 30 carbon atoms that may be optionally substituted with a substituent, and preferably, a primary saturated hydrocarbon chain group. The alkyl group may be a straighten chain or branched group, and preferably a straighten chain alkyl group. Specifically, a C8-C30 primary alkyl group is preferable, and a C12-C22 primary alkyl group is more preferable, and a C16-C20 primary alkyl group is further more preferable. Preferred one specific examples thereof include a C18 primary alkyl group. For the substituent, the kind thereof is not limited as long as it does not disturb any reactions used in the present invention (for example, a capping reaction, a coupling reaction in an oligonucleotide synthesis, a deprotection reaction, a deblocking reaction, an oxidative reaction, and a sulfidation reaction), and include, for example, one or more groups selected from a C—C6 alkyl group and a C3-C6 cycloalkyl group, and preferably a C1-C6 alkyl group. Specific examples of the substituent include methyl, ethyl, isopropyl, cyclopropyl, and cyclohexyl.

The term of "(an) optionally substituted C1-C6 alkyl group" for $R^6$ as used herein represents a saturated hydrocarbon chain group containing 1 to 6 carbon atoms. The alkyl group may be straighten or branched. Examples of the optionally substituted C1-C6 alkyl group include preferably a C3 alkyl group. Preferred one specific example include methyl. For the substituent, the kind thereof is not limited as long as it does not disturb any reactions used in the present invention (for example, a capping reaction, a coupling reaction in an oligonucleotide synthesis, a deprotection reaction, a deblocking reaction, an oxidative reaction, and a sulfidation reaction), and include, for example, one or more groups selected from a C1-C3 alkyl group and a C3-C6 cycloalkyl group.

The term of "(an) optionally substituted C3-C6 cycloalkyl group" for $R^6$ as used herein represents a C3 to C6 saturated alicyclic hydrocarbon group. For the substituent, the kind thereof is not limited as long as it does not disturb any reactions used in the present invention (for example, a capping reaction, a coupling reaction in an oligonucleotide synthesis, a deprotection reaction, a deblocking reaction, an oxidative reaction, and a sulfidation reaction), and include, for example, a C1-C3 alkyl group. Specific examples of the cycloalkyl group include cyclopropyl, cyclobutyl, cyclopentyl, and cyclohexyl.

The term of "(an) optionally substituted C1-C6 alkylene group" for $R^7$ and $R^8$ as used herein represents a divalent group of a saturated hydrocarbon group containing 1 to 6 carbon atoms. The alkylene group may be straighten or branched. Examples of the optionally substituted C1-C6 alkylene group include preferably a C1-C4 alkylene group, and more preferably a C1-C3 alkylene group. Specific examples thereof include methylene, ethylene, trimethylene (propylene), tetramethylene (n-butylene) and the like. For the substituent, the kind thereof is not limited as long as it does not disturb any reactions used in the present invention (for example, a capping reaction, a coupling reaction in an oligonucleotide synthesis, a deprotection reaction, a deblocking reaction, an oxidative reaction, and a sulfidation reaction), and include, for example, one or more groups selected from a C1-C3 alkyl group, a C3-C6 cycloalkyl group, a C6-C10 aryl group. Specific examples of the substituent include methyl, ethyl, isopropyl, phenyl, and the like.

The term of "(an) optionally substituted C1-C6 alkyleneoxy group" for $R^7$ as used herein represents the above-mentioned "(an) optionally substituted C1-C6 alkylene group" which is attached to an oxygen atom. Specific examples thereof include methyleneoxy, ethyleneoxy, trimethyleneoxy (propyleneoxy), and the like.

The term of "(an) optionally substituted non-aromatic heterocyclic group" for $R^6$, $R^7$ and $R^8$ as used herein represents a 4 to 8 membered monocyclic or bicyclic non-aromatic heterocyclic group containing 1 to 4 heteroatoms (preferably 1 to 2 heteroatom(s), more preferably 1 heteroatom) selected from sulfur atom, oxygen atom and nitrogen atom (preferably oxygen atom or nitrogen atom, more preferably nitrogen atom). The optionally substituted non-aromatic heterocyclic group may be fused to cycloalkyl ring, aromatic hydrocarbon cycle, or aromatic heterocycle. Specific examples of the optionally substituted non-aromatic heterocyclic group include azetidinyl, pyrrolidinyl, tetrahydrofuranyl, imidazolidinyl, thiazolidinyl, isothiazolidinyl, piperidinyl, piperazinyl, morpholinyl, thiomorpholinyl, tetrahydropyranyl, homopiperazinyl, homomorpholinyl, 3-azabicyclo[3.1.0]hexyl, and 3-azabicyclo[3.1.1]octyl, and include preferably piperidinyl, piperazinyl, 3-azabicyclo[3.1.1]octyl and the like. For the substituent, the kind thereof is not limited as long as it does not disturb any reactions used in the present invention (for example, a capping reaction, a coupling reaction in an oligonucleotide synthesis, a deprotection reaction, a deblocking reaction, an oxidative reaction, and a sulfidation reaction), and include, for example, one or more groups selected from a C1-C3 alkyl group and a C3-C6 cycloalkyl group. Specific examples of the substituent include methyl, ethyl, isopropyl, cyclopropyl, and the like.

The term of "(an) optionally substituted aryl group (or an optionally substituted aromatic hydrocarbon cyclic group)" for $R^6$, $R^7$ and $R^8$ as used herein represents a monocyclic or bicyclic aromatic hydrocarbon cyclic group. The optionally substituted aryl group represents a six (6)-ten (10) membered monocyclic or bicyclic aromatic hydrocarbon cyclic group. The optionally substituted aryl group may be fused to a cycloalkyl ring, a non-aromatic heterocycle, or an aromatic heterocycle. Specific examples of the optionally substituted aryl group include phenyl, indenyl, naphthyl, cyclohexanophenyl, pyrrolidine-fused phenyl (indoline), piperidine-fused phenyl and the like, and include preferably phenyl. For the substituent, the kind thereof is not limited as long as it does not disturb any reactions used in the present invention (for example, a capping reaction, a coupling reaction in an oligonucleotide synthesis, a deprotection reaction, a deblocking reaction, an oxidative reaction, and a sulfidation reaction), and include, for example, one or more groups selected from a C1-C3 alkyl group and a C3-C6 cycloalkyl group. Specific examples of the substituent include methyl, ethyl, isopropyl, cyclopropyl, and the like.

The term of "(an) optionally substituted heteroaryl group (or optionally substituted aromatic heterocyclic group)" for $R^6$, $R^7$ and $R^8$ as used herein represents a 5 to 10 membered monocyclic or bicyclic aromatic heterocyclic group containing 1 to 4 heteroatoms (preferably 1 to 2 heteroatom(s), more preferably 1 heteroatom) selected from sulfur atom, oxygen atom and nitrogen atom (preferably oxygen atom or nitrogen atom, more preferably nitrogen atom). The optionally substituted heteroaryl group may be fused to cycloalkyl ring, non-aromatic heterocycle, or aromatic hydrocarbon cycle. Specific examples of the optionally substituted heteroaryl group include pyrrolyl, furanyl, thienyl, imidazolyl, pyrazolyl, oxazolyl, isoxazolyl, thiazolyl, triazolyl, tetrazolyl, oxadiazolyl, pyridinyl, pyrazinyl, pyrimidinyl, pyridazinyl, thiazinyl, triazinyl, indolyl, quinolyl, isoquinolyl, isoindolyl, benzimidazolyl, and the like, and include preferably pyridinyl, pyrazinyl, pyrimidinyl, isoquinolyl, benzimidazolyl, and the like. For the substituent, the kind thereof is not limited as long as it does not disturb any reactions used in the present invention (for example, a capping reaction, a coupling reaction in an oligonucleotide synthesis, a deprotection reaction, a deblocking reaction, an oxidative reaction, and a sulfidation reaction), and include, for example, one or more groups selected from a C1-C3 alkyl group and a C3-C6 cycloalkyl group. Specific examples of the substituent include methyl, ethyl, isopropyl, cyclopropyl, and the like.

The term of "(an) optionally substituted aralkyl group)" for $R^6$, $R^7$ and $R^8$ as used herein represents a group in which the above-mentioned optionally substituted aryl group is attached to the above-mentioned optionally substituted alkyl group. Specific examples of the optionally substituted aralkyl group include benzyl, phenethyl, and the like, and include preferably benzyl. Examples of the substituent include the above-mentioned substituents that are referred to in the above-mentioned optionally substituted alkyl group and the above-mentioned optionally substituted aryl group.

The term of "(an) optionally substituted heteroaryl alkyl group" for $R^6$, $R^7$ and $R^8$ as used herein represents a group in which the above-mentioned optionally substituted heteroaryl group is attached to the above-mentioned optionally substituted alkyl group. Specific examples of the optionally substituted heteroaryl alkyl group include pyridylmethyl and pyridylethyl, and the like, and include preferably pyridylmethyl. Examples of the substituents thereof include the substituents that are referred to in the above-mentioned optionally substituted alkyl group and the above-mentioned optionally substituted heteroaryl group.

The term of "(an) optionally substituted non-aromatic heterocyclic alkyl group" for $R^6$, $R^7$ and $R^8$ as used herein represents a group in which the above-mentioned optionally substituted non-aromatic heterocyclic group is attached to the above-mentioned optionally substituted alkyl group. Specific examples of the optionally substituted non-aromatic heterocyclic alkyl group include piperidinylmethyl, piperidinylethyl, piperadinylmethyl, and piperadinylethyl, and include preferably piperadinylmethyl. Examples of the substituents thereof include the substituents that are referred to in the above-mentioned optionally non-aromatic heterocyclic group and the above-mentioned optionally substituted alkyl group.

According to one embodiment of the present invention, examples of the soluble part in the above-mentioned formula (II) include the part wherein the moiety represented by the following formula (IV):

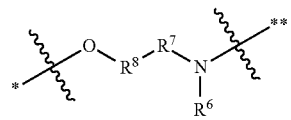

(wherein,
* represents a binding position to L;
** represents a binding position to a carbonyl group; and
each of $R^6$, $R^7$ and $R^8$ is the same as defined in the formula (II))
is a moiety represented by the following structural formula:

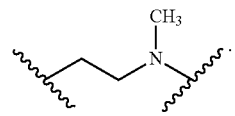 [SMILES: *CCN(*)C]

According to one embodiment of the present invention, the present invention provides a nucleotide containing the above-mentioned pseudo solid phase protecting group, and provides a nucleotide represented by the following formula (III):

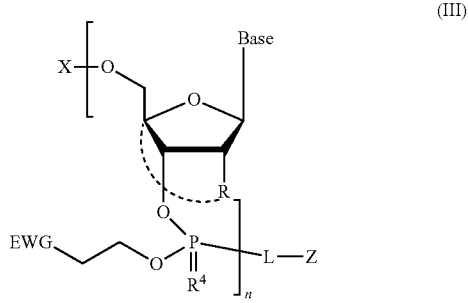

[wherein,
Z represents a psuedo solid phase protecting group represented by the above-mentioned formula (II), L represents a linker;

Base each independently represents an optionally protected nucleic acid base, the number of n of EWG each independently represents an electrophilic group, the number of n of $R^4$ each independently represents an oxygen atom or a sulfur atom, the number of n of R each independently represents a hydrogen atom, a halogen atom, a hydroxy group optionally substituted with a protecting group, an optionally substituted C1-C6 alkoxy group, an organic group for bridging to 4'-carbon atom, or a bridge structural of artificial nucleic acid group, n is an arbitrary integer of 0 or more, and X represents a temporary protecting group which can be deprotected with an acid.]

The term of "hydrogen atom" for R used herein represents a fluorine atom, a chlorine atom, a bromine atom, and an iodine atom, and preferably a fluorine atom.

The substituent in the term of "hydroxyl group optionally substituted with a protecting group" for R as used herein may be a protecting group which is usually known to be used in an oligonucleotide synthesis, and includes a silyl type protecting group (such as TOM group (—$CH_2$ OSi(iPr)$_3$).

Examples of the substituents in the term of "(an) optionally substituted C1-C6 alkoxy group" for R as used herein include a C1-C6 alkoxy group, and specific examples thereof include 2-methoxyethoxy group.

The term of "organic group bridged to 4-carbon atom" include 4'-C1-C6 alkoxy-2' group, and for example, 4'-$CH_2CH_2O$-2' group.

The term of "electrophilic group (abbreviated as EWG)" as used herein represents a substituent having a property of diminishing an electron density which is in general used in an organic chemistry. Specific examples thereof include carboxyl group, halogen atom, nitro group, and ester group, which is not limited thereto.

The term of "temporary protecting group which is removable with an acid" as used herein represents a temporary protecting group which is removable under an acidic condition for 5'-hydroxy group as used herein.

As used herein, L in the formula (III) represents a linker, which represents a divalent group in which the (oligo) nucleotide molecule is linked to the pseudo solid phase protecting group. The linker is not limited unless specified, as long as it does not disturb any reactions used in the present invention (for example, a capping reaction, a coupling reaction in an oligonucleotide synthesis, a deprotection reaction, a deblocking reaction, an oxidative reaction, and a sulfidation reaction).

The definition of "n" is an integer of 2 to 100, preferably 10 to 40.

As used herein, according to one embodiment, L represents a linker which is any one of residue selected from the group consisting of the following formulae:

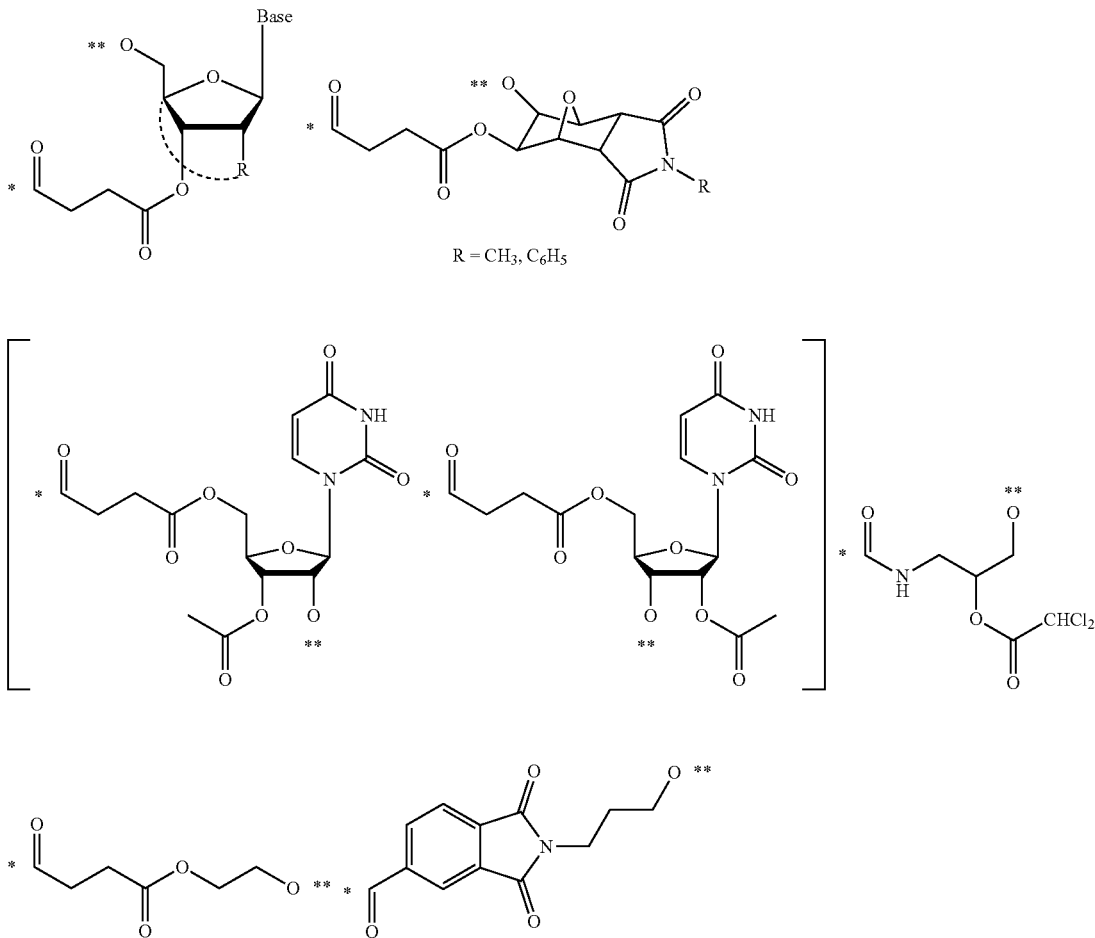

[wherein,

* represents a binding position to a hydrophobic group, and ** represents a binding position to a phosphorus atom, Base each independently represents an optionally protected nucleic acid base, and R each independently represents a hydrogen atom, a halogen atom, a hydroxy group optionally substituted with a protecting group, an optionally substituted C1-C6 alkoxy group, an organic group for bridging to 4'-carbon atom, or a bridge structural of artificial nucleic acid group.]

Preferably, L represents a group selected from any one of the following formulae:

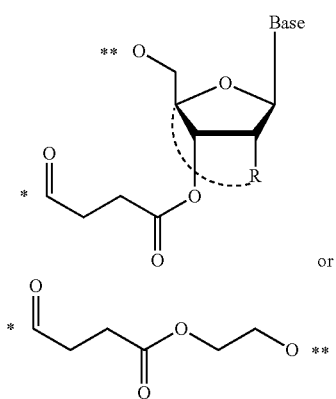

As used herein, according to one embodiment, specific examples of nucleotide compound represented by formula (III) include a tetramer (N=4) represented by the following formula, which is not limited thereto.

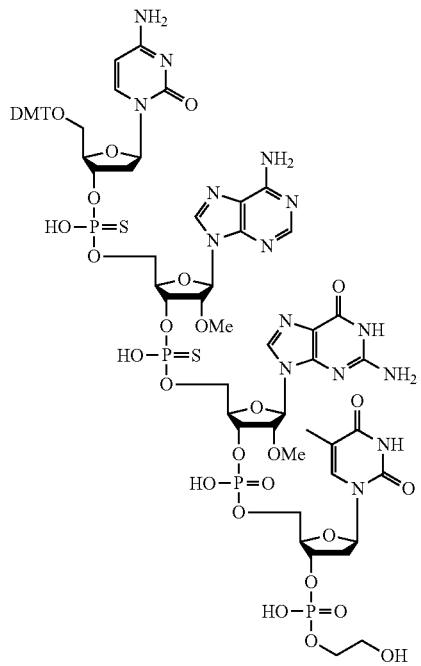

A nucleotide containing the above-mentioned pseudo solid phase protecting group may be used as a raw material for the preparation method of oligonucleotide of the present invention or a starting material for 1 cycle of nucleotide elongation.

In the preparation of the oligonucleotide preparation, a series of total steps in which one nucleotide is extended (referred to as "1 cycle of nucleotide elongation") can be conducted optionally by comprising one or two purification step(s).

One Cycle of Nucleotide Elongation in a Preparation of Oligonucleotide (Twice Purification)
First Stage
 i) solubilizing 5'-OH terminal n-mer in a solvent,
 ii) reacting the 5'-OH terminal n-mer, the m+1-phosphoramidite compound, and an activator in a solvent to conduct a coupling reaction.

The proceedings of a reaction is confirmed by disappearing $HO(Nps)_n$-SR (disappearance of $HO(Nps)_n$-SR).

iii) after the coupling reaction, reacting the reaction product with a capping reaction reagent of the present invention to conduct a capping reaction.
 iv) after the capping reaction, treating the resulting reaction mixture with a nucleophile (for example, alcohol such as ethanol) to obtain a coupling crude product.
 v) reacting the coupling reaction product with a sulfuring reagent in a solvent containing an organic base (for example, pyridine). Next, after reacting the reaction product with a phosphite compound, the reaction product is precipitated out by using alcohol (for example, methanol) to an intermediate compound DMT-$(Nps)_{m+1+n}$-SR.

Second Stage
 vi) precipitating out the obtained intermediate compound DMT-$(Nps)_{n+1}$-SR by using a solvent containing a pyrrole and an acid or a pyridine and alcohol (for example, methanol) to obtain the desired HO-$(Nps)_{n+1}$-SR.

One Cycle of Nucleotide Elongation in a Preparation of Oligonucleotide (Once Purification)
First Stage
 i) Solubilizing 5'-OH terminal n-mer in a solvent,
 ii) reacting the 5'-OH terminal n-mer, the m+1-phosphoramidite compound, and an activator in a solvent to conduct a coupling reaction.

The proceedings of a reaction is confirmed by disappearing $HO(Nps)_n$-SR (disappearance of HO(Nps)n-SR).

iii) after the coupling reaction, reacting the reaction product with a capping reaction reagent of the present invention to conduct a capping reaction.
 iv) after the capping reaction, treating the resulting reaction mixture with a nucleophile (for example, alcohol such as ethanol) to obtain a coupling crude product.
 v) reacting the coupling reaction product with a sulfuring reagent in a solvent containing an organic base (for example, pyridine). Next, after reacting the reaction product with a phosphite compound, the reaction product is precipitated out by using alcohol (for example, methanol) to an intermediate compound DMT-$(Nps)_{m+1+n}$-SR.

(Kit)

According to one embodiment of the present invention, the present invention provides also a kit for preparation and purification of (oligo)nucleotide, for example. The kit of the present invention comprises as an ingredient at least one of capping reaction reagent of the present invention. According to one embodiment of the present invention, the kit of the present invention comprises (a) a capping reaction reagent of the present invention; (b) a nucleophile; (c) at least one of (oligo)nucleotide, for example, a phosphoramidite compound of (oligo)nucleotide; (d) at least one of extensible (oligo)nucleotide compound; (e) at least one of activator that can be used to extend the oligonucleotide; (f) at least one of buffer; (g) a package describing an procedure explanation for extending (oligo)nucleotide by using a kit ingredient; as well as (h) at least one of container for fulfilling with kit ingredients.

Examples of "buffer" as used herein include anything usually used as long as it does not affect any adverse effect (such as deposition of kit ingredient(s), or inhibition of a reaction).

Also according to one embodiment of the present invention, a kit of the present invention is a kit for a capping reaction of (oligo)nucleotide, which comprises (a) a capping reaction reagent of the present invention; (b) a nucleophile; (g) a package describing an procedure explanation for capping (oligo)nucleotide by using kit ingredients; as well as (h) at least one of container for fulfilling with kit ingredients.

EXAMPLES

Examples of the present invention are described as example of the present invention below, which is not limited thereto.

The reagent was as needed, obtained as a commercially available products, or was prepared according to a publicly known method. Also, as each of measuring device, a usually used device was applied.

Synthesis of Highly Liposoluble Phosphoramidite

Example 1

Preparation of 2-Cyanoethyl Octadecyl Diisopropyl Phosphoramidite

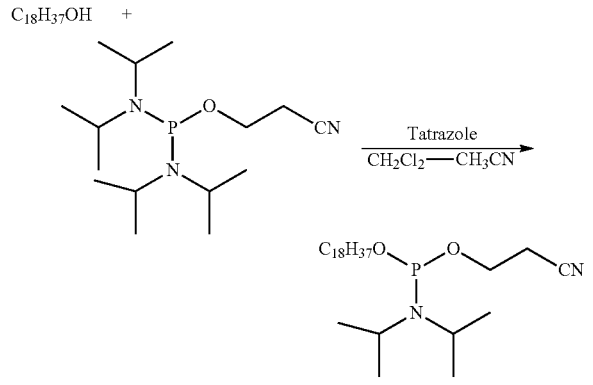

Under argon atmosphere, to octadecanol 541 mg and tetrazole 141 mg were added dehydrated dichloromethane 2.4 mL and acetonitrile 1.6 mL, and the mixture was solubilized with stirring, and thereto was added dropwise 3-(bis(diisopropylamino)phoshinoxy)propanenitrile (0.70 mL, 2.2 mmol), and the mixture was stirred for 1 hour. The reaction solutions were transferred to a separatory funnel while washing thoroughly with dichloromethane 5 L, washed with water 10 mL, and the organic layer was concentrated under reduced pressure. To the concentrated reaction mixture was added hexane 20 mL, and 100 μL of the mixture was pull out, and thereto were added 0.1M triphenyl phosphine in dichloromethane solution 100 μL and CDCl₃ 40 μL to make a NMR sample without washing. Twenty (20) mL of hexane was transferred into a separatory funnel and washed with acetonitrile 20 mL, and the organic layer was transferred to a graduated cylinder. To the resulting hexane solution 18 mL was added hexane 2 mL, and 100 μL portion was pull out from the hexane solution 20 mL, and separately, 0.1M triphenyl phosphine in dichloromethane solution 100 μL was pull out, and thereto was added CDCl₃ 400 μL to make a NMR sample for washing once. The resulting hexane solution 20 mL was transferred to a separatory funnel, and the resulting solution was washed with acetonitrile 20 mL, and the organic layer was transferred to a graduated cylinder. To the resulting hexane solution 17 mL was added hexane 3 mL to prepare hexane solution 20 mL, and 100 μL portion was pull out from the hexane solution, and separately, thereto were added 0.1M triphenyl phosphine in dichloromethane solution 100 μL and CDCl₃ 400 μL were added thereto to make a NMR sample for washing twice. The organic layer was concentrated under reduced pressure with evaporator to 2-cyanoethyl octadecyl diisopropyl phosphoramidite as colorless oil 682 mg.

$^1$H-NMR (400 MHz CDCl₃); δ 0.88 (t, 3H, J=7.2 Hz), 1.15-1.19 (m, 12H), 1.25-1.34 (m, 90H), 1.58-1.62 (m, 2H), 2.64 (t, 2H, J=6.4 Hz), 3.55-3.65 (m, 4H), 3.80-3.85 (m, 2H)
$^{31}$P-NMR (162 MHz CDCl₃); δ 146.77

Example 2

Preparation of 2-Cyanoethyl Octadecyl Diisopropyl Phosphoramidite (50 Mmol Scale)

Under argon atmosphere, to octadecanol 13.52 g and tetrazole 1.93 g were added dehydrated dichloromethane 60 mL and acetonitrile 40 mL, and the mixture was solubilized with stirring, and thereto was added dropwise 3-(bis(diisopropylamino)phoshinoxy)propanenitrile (17.5 mL), and the mixture was stirred for 1 hour. The reaction solutions were transferred to a separatory funnel while washing thoroughly with dichloromethane, washed with water, and the organic layer was concentrated under reduced pressure. To the concentrated reaction mixture was added hexane, and the mixture was washed with acetonitrile twice. The hexane layer was concentrated with an evaporator under reduced pressure to obtain 2-cyanoethyl octadecyl diisopropyl phosphoramidite as colorless oil 20.7 g.

Example 3

Preparation of 2-Cyanoethyl Octadecyl Diisopropyl Phosphoramidite (In the Case where 2-Cyanoethyl Diisopropyl Chlorophosphoramidite is Used as a Trivalent Phosphorus Compound)

Under argon atmosphere, to octadecanol 811 mg and diisopropylethylamine 1.04 mL were added dehydrated tetrahydrofuran 6 mL, and the mixture was solubilized with stirring and ice-cooled, and thereto was added dropwise 2-cyanoethyl diisopropylchlorophosphoramidite (0.74 mL), and the mixture was stirred for 1 hour. The reaction solutions were transferred to a separatory funnel while washing thoroughly with dichloromethane, washed with water, and the organic layer was concentrated under reduced pressure. To the concentrated reaction mixture was added hexane, and the mixture was washed acetonitrile twice. The hexane layer was concentrated with an evaporator under reduced pressure to obtain 2-cyanoethyl octadecyl diisopropyl phosphoramidite as colorless oil 1.08 g.

Example 4

Preparation of 2-Cyanoethyl Decyl Diisopropyl Phosphoramidite

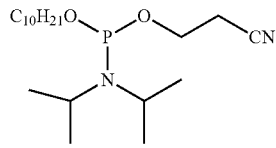

Under argon atmosphere, to octadecanol 381 μL and tetrazole 141 mg were added dehydrated dichloromethane 2.4 mL and acetonitrile 1.6 mL, and the mixture was solubilized with stirring, and thereto was added dropwise 3-(bis(diisopropylamino)phosphinoxy)propanenitrile (0.70 mL, 2.2 mmol) dropwise, and the mixture was stirred for 1 hour. The reaction solutions were transferred into a separatory funnel while washing thoroughly with dichloromethane 5 mL, washed with water 10 mL, and the organic layer was concentrated under reduced pressure. To the concentrated reaction mixture was added hexane 20 mL, and 100 μL of the mixture was pull out, and thereto were added 0.1M triphenyl phosphine in dichloromethane solution 100 μL and CDCl$_3$ 40 μL to make a NMR sample without washing. Twenty (20) mL of hexane solution was transferred into a separatory funnel and washed with acetonitrile 20 mL, and the organic layer was transferred to a graduated cylinder. To the resulting hexane solution 18 mL was added hexane 2 mL, and 100 μL portion was pull out from the hexane solution 20 mL, and separately, 0.1 M triphenyl phosphine in dichloromethane solution 100 μL was pull out, and thereto was added CDCl$_3$ 400 μL to make a NMR sample for washing once. The resulting hexane solution 20 mL was transferred to a separatory funnel, and the resulting solution was washed with acetonitrile 20 mL, and the organic layer was transferred to a graduated cylinder. To the resulting hexane solution 17 mL was added hexane 3 mL to prepare hexane solution 20 mL, and 100 μL portion was pull out from the hexane solution, and separately, thereto were added 0.1M triphenyl phosphine in dichloromethane solution 100 μL and CDCl$_3$ 400 μL were added thereto to make a NMR sample for washing twice. The organic layer was concentrated under reduced pressure with evaporator to 2-cyanoethyl decyl diisopropyl phosphoramidite as colorless oil 203 mg.

$^1$H-NMR (400 MHz CDCl$_3$); δ 0.88 (t, 3H, J=7.2 Hz), 1.15-1.19 (m, 12H), 1.25-1.34 (m, 14H), 1.58-1.62 (m, 2H), 2.64 (t, 2H, J=6.4 Hz), 3.55-3.65 (m, 4H), 3.79-3.84 (m, 2H)

$^{31}$P-NMR (162 MHz CDCl$_3$); δ 146.75

Example 5

Preparation of 2-Cyanoethyl Octyl Diisopropyl Phosphoramidite

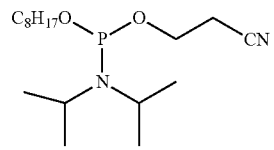

Under argon atmosphere, to octadecagon 314 μL and tetrazole 141 mg were added dehydrated dichloromethane 2.4 mL and acetonitrile 1.6 mL, and the mixture was solubilized with stirring, and thereto was added dropwise 3-(bis(diisopropylamino)phosphinoxy)propanenitrile (0.70 mL, 2.2 mmol) dropwise, and the mixture was stirred for 1 hour. The reaction solutions were transferred into a separatory funnel while washing thoroughly with dichloromethane 5 mL, washed with water 10 mL, and the organic layer was concentrated under reduced pressure. To the concentrated reaction mixture was added hexane 20 mL, and 100 μL of the mixture was pull out, and thereto were added 0.1M triphenyl phosphine in dichloromethane solution 100 μL and CDCl$_3$ 40 μL to make a NMR sample without washing. Twenty (20) mL of hexane solution was transferred into a separatory funnel and washed with acetonitrile 20 mL, and the organic layer was transferred to a graduated cylinder. To the resulting hexane solution 18 mL was added hexane 2 mL, and 100 μL portion was pull out from the hexane solution 20 mL, and separately, 0.1 M triphenyl phosphine in dichloromethane solution 100 μL was pull out, and thereto was added CDCl$_3$ 400 μL to make a NMR sample for washing once. The resulting hexane solution 20 mL was transferred to a separatory funnel, and the resulting solution was washed with acetonitrile 20 mL, and the organic layer was transferred to a graduated cylinder. To the resulting hexane solution 17 mL was added hexane 3 mL to prepare hexane solution 20 mL, and 100 μL portion was pull out from the hexane solution, and separately, thereto were added 0.1M triphenyl phosphine in dichloromethane solution 100 μL and CDCl$_3$ 400 μL were added thereto to make a NMR sample for washing twice. The organic layer was concentrated under reduced pressure with evaporator to 2-cyanoethyl decyl diisopropyl phosphoramidite as colorless oil 54 mg.

Example 6

Preparation of 2-Cyanoethyl Hexyl Diisopropyl Phosphoramidite

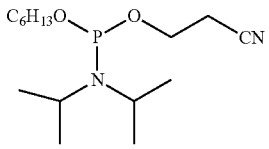

Under argon atmosphere, to hexanol 249 μL and tetrazole 141 mg were added dehydrated dichloromethane 2.4 mL and acetonitrile 1.6 mL, and the mixture was solubilized with stirring, and thereto was added dropwise 3-(bis(diisopropylamino)phosphinoxy)propanenitrile (0.70 mL, 2.2 mmol) dropwise, and the mixture was stirred for 1 hour. The reaction solutions were transferred into a separatory funnel while washing thoroughly with dichloromethane 5 mL, washed with water 10 mL, and the organic layer was concentrated under reduced pressure. To the concentrated reaction mixture was added hexane 20 mL, and 100 μL of the mixture was pull out, and thereto were added 0.1M triphenyl phosphine in dichloromethane solution 100 μL and CDCl₃ 40 μL to make a NMR sample without washing. Twenty (20) mL of hexane solution was transferred into a separatory funnel and washed with acetonitrile 20 mL, and the organic layer was transferred to a graduated cylinder. To the resulting hexane solution 18 mL was added hexane 2 mL, and 100 μL portion was pull out from the hexane solution 20 mL, and separately, 0.1 M triphenyl phosphine in dichloromethane solution 100 μL was pull out, and thereto was added CDCl₃ 400 μL to make a NMR sample for washing once. The resulting hexane solution 20 mL was transferred to a separatory funnel, and the resulting solution was washed with acetonitrile 20 mL, and the organic layer was transferred to a graduated cylinder. To the resulting hexane solution 17 mL was added hexane 3 mL to prepare hexane solution 20 mL, and 100 μL portion was pull out from the hexane solution, and separately, thereto were added 0.1M triphenyl phosphine in dichloromethane solution 100 μL and CDCl₃ 400 μL were added thereto to make a NMR sample for washing twice. The organic layer was concentrated under reduced pressure with evaporator to 2-cyanoethyl hexyl diisopropyl phosphoramidite as colorless oil 24 mg.

A recovery yield of the phosphoramidite compound (monoamidite compound) contained in the organic solutions, the organic solutions being obtained by a purification procedure (including extraction and washing procedures) of the phosphoramidite compounds prepared in the above-mentioned examples 1 to 6, is summarized in the below-mentioned Table 1 and FIG. 1.

TABLE 1

| | | Recovery ratio | | |
|---|---|---|---|---|
| Ex No. | Product | Washing sample | Monoamidite[*1] | Diamidite[*1] |
| Ex No.1 | C18 product | Washing once | 93.7% | 0.0% |
| | | Washing twice | 88.7% | 0.0% |
| Ex No.4 | C10 product | Washing once | 65.4% | 33.3% |
| | | Washing twice | 31.4% | 0.0% |
| Ex No.5 | C8 product | Washing once | 33.3% | 20.9% |
| | | Washing twice | 11.5% | 0.0% |
| Ex No.6 | C6 product | Washing once | 23.8% | 0.0% |
| | | Washing twice | 5.2% | 0.0% |

[*1]These values were determined from an integrated value in NMR data of the samples after adding a prescribed amount of triphenyl phosphine to these compounds as an internal standard.

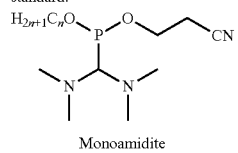

Monoamidite

TABLE 1-continued

| | | Recovery ratio | | |
|---|---|---|---|---|
| Ex No. | Product | Washing sample | Monoamidite[*1] | Diamidite[*1] |

Diamidite

It can be found from the results of Table 1 and FIG. 1 that according to the preparation and purification method of the present invention, a phosphoramidite product (monoamidite compound) with substantial high purity, which does not contain a H-phosphonate compound and a diamidite compound which provide by-products at a capping procedure in high yield by extracting and washing the reaction mixture with organic solvents depending on increasing of a liposolubility of the phosphoramidite compound.

Example 7

Preparation of 2-cyanoethyl 2'-octyldodecanyl Diisopropyl Phosphoramidite

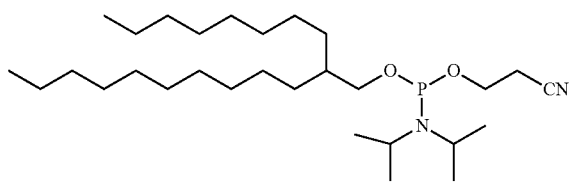 [SMILES: CCCCCCCCCCC(CCCCCCCC)COP(OCCC#N)N(C(C)C)C(C)C]

Under argon atmosphere, to 2-octyldodecanol 3.56 mL and ETT 0.72 g were added dehydrated dichloromethane 12 mL and acetonitrile 8 mL, and the mixture was solubilized with stirring, and thereto was added dropwise 3-(bis(diisopropylamino)phoshinoxy)propanenitrile (3.5 mL), and the mixture was stirred for 1 hour. The reaction solutions were transferred to a separatory funnel while washing thoroughly with dichloromethane, washed with water, and the organic layer was concentrated under reduced pressure. To the concentrated reaction mixture was added hexane, and the mixture was washed with acetonitrile twice. The hexane layer was concentrated with an evaporator under reduced pressure to obtain 2-cyanoethyl octadecyl diisopropyl phosphoramidite as colorless oil 3.43 g.

¹H-NMR (400 MHz CDCl₃); δ 0.88 (t, 6H, J=7.2 Hz), 1.16-1.19 (m, 12H), 1.2-1.4 (m, 32H), 1.54 (m, 1H), 2.63 (t, 2H, 6.4 Hz), 3.43-3.49 (m, 1H), 3.52-3.62 (m, 3H), 3.78-3.86 (m, 2H)

³¹P-NMR (162 MHz CDCl₃); δ 146.90

Example 8

Preparation of Phy-CE-Phosphoramidite

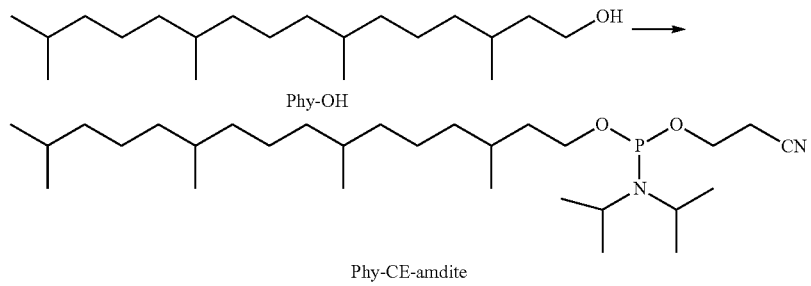

Under argon atmosphere, to the compound Phy-OH 2.98 g and tetrazole 0.39 g were added dehydrated dichloromethane 12 mL and acetonitrile 8 mL, and the mixture was solubilized with stirring, and thereto was added dropwise 3-(bis(diisopropylamino)phoshinoxy)propanenitrile (3.5 mL), and the mixture was stirred for 1 hour. The reaction solutions were transferred to a separatory funnel while washing thoroughly with dichloromethane, washed with water, and the organic layer was concentrated under reduced pressure. To the concentrated reaction mixture was added hexane, and the mixture was washed with acetonitrile twice. The hexane layer was concentrated with an evaporator under reduced pressure to obtain the compound Phy-CE-amidite as colorless oil 3.84 g.

$^1$H-NMR (400 MHz CDCl$_3$); δ 0.88-0.99 (m, 15H), 1.01-1.16 (m, 8H), 1.16-1.21 (m, 12H), 1.21-1.32 (m, 9H), 1.32-1.45 (m, 4H), 1.49-1.55 (m, 2H), 1.55-1.73 (m, 1H), 2.64 (t, 2H, 6.4 Hz), 3.55-3.72 (m, 4H), 3.73-3.79 (m, 2H)
$^{31}$P-NMR (162 MHz CDCl$_3$); δ 147.13, 147.22

Example 9

Synthesis of Ethylene Glycolate Compound and Analogous Compounds Thereof

A synthetic scheme of an ethylene glycolate compound or analogous compounds thereof are shown in the below-mentioned Reaction Scheme III.

Reaction Scheme III

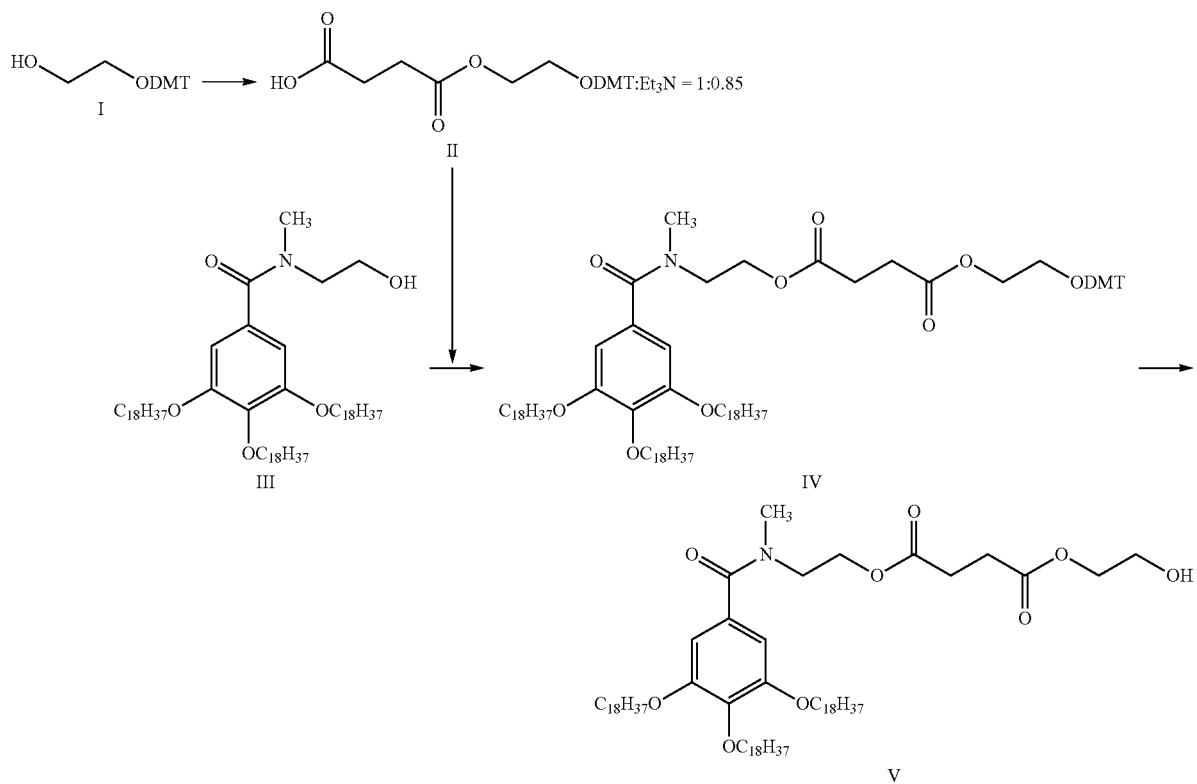

(Preparation of Compound II)

The compound I 8.12 g was solubilized in dehydrated dichloromethane 35 mL, and to the solution were added triethylamine 14.9 mL and succinic anhydride 4.46 g. The mixture was stirred at room temperature overnight, and thereto was added methanol 2.2 mL, and the mixture was further stirred overnight. The resulting mixture solution was washed with a phosphate triethylamine buffer (pH about 6.8) and the mixed solution was then concentrated under reduced pressure, followed by evaporating under reduced pressure overnight to remove volatile component to obtain the compound II 11.1 g. The existence ratio of triethylamine was approximated from $^1$H NMR integrated value.

$^1$H-NMR (400 MHz CDCl$_3$); δ 1.20 (t, 7.7H, J=7.2 Hz), 2.58 (t, 2H, J=6.8 Hz), 2.68 (t, 2H, J=6.8 Hz), 2.94 (q, 5.1H, J=7.2 Hz), 3.25 (t, 2H, J=5.0 Hz), 3.79 (s, 6H), 4.23 (t, 2H, J=5.0 Hz), 6.80-6.85 (m, 4H), 7.15-7.21 (m, 1H), 7.27-7.36 (m. 6H), 7.44-7.46 (m. 2H), 9.65 (brs, 1.9H)

(Preparation of Compound III)

A synthesis of compound III was conducted according to the method described in JP 2001-2533986 A1.

(Preparation of Compound IV)

A mixture of the compound III 15.7 g, the compound II 10.6 g, and the dehydrated toluene 100 mL was concentrated under reduced pressure to dryness. To the residue was added dehydrated chloroform 100 mL, and thereto were added further diisopropylethylamine 4.35 mL, HBTU 9.47 g and DMAP 3.05 g. The mixture was stirred at 45° C. overnight. To the resulting reaction mixture was added methanol 100 mL, and the mixture was concentrated under reduced pressure. The resulting solids were filtered, washed with methanol, and concentrated under reduced pressure. The resulting mixture with dehydrated toluene 100 mL was concentrated under reduced pressure to dryness. To the residue was added chloroform 100 mL, and further added 2,4,6-trimethylpyridine 45 mL, 1-methyl imidazole 30 mL and acetic anhydride 30 mL, and the mixture was stirred overnight. To the resulting reaction mixture was added methanol 100 mL, and the mixture was concentrated under reduced pressure. The resulting solids were filtered, washed with methanol, and concentrated under reduced pressure to obtain the compound IV as a desired product 22.67 g. The products were concluded to be completely esterified from a NMR measurement result and a quantitative measurement result with dimethoxy trityl cation (λ=498 s=7.0*10$^-$4): 725 μmol/g (theoretical value 704 μmol/g).

$^1$H-NMR (400 MHz CDCl$_3$); δ 0.88 (t, 9H, J=7.0 Hz), 1.15-1.39 (m, 84H), 1.40-1.51 (m, 6H), 1.68-1.85 (m, 6H), 2.69 (s, 4H), 3.04 (s, 3H) 3.27 (t, 2H, J=5.0 Hz), 3.5-3.82 (m, 2H) 3.79 (s, 6H), 3.93-3.98 (m, 6H), 4.26 (t, 2H, J=5.0 Hz), 4.30-4.43 (m, 2H), 6.57 (s, 2H), 6.80-6.85 (m, 4H), 7.17-7.22 (m, 1H), 7.26-7.34 (m. 6H), 7.42-7.46 (m. 2H)

(Preparation of Compound V)

The compound IV 19.8 g was solubilized in dichloromethane 550 mL, and to the solubilized solution were added pyrrole 12.8 mL and dichloroacetic acid 18.3 mL. The mixture was filtered at room temperature for 15 minutes, and to the reaction mixture were added methanol 332 mL and pyridine 26.8 mL. The reaction mixture was concentrated under reduced pressure, and the resulting solids were filtered, washed with methanol and concentrated under reduced pressure to obtain the compound V as a desired product 15.6 g.

$^1$H-NMR (400 MHz CDCl$_3$); δ 0.88 (t, 9H, J=6.8 Hz), 1.15-1.39 (m, 84H), 1.41-1.51 (m, 6H), 1.68-1.85 (m, 6H), 2.54 (brs, 1H), 2.66 (s, 4H), 3.05 (s, 3H) 3.5-3.81 (m, 2H) 3.81 (dd, 2H, J=9.2, 6.0 Hz), 3.94-3.99 (m, 6H), 4.23 (dd, 2H, J=9.2, 6.0 Hz), 4.10-4.48 (m, 2H), 6.58 (s, 2H)

Example 10

Synthesis of Oligonucleotide

A synthetic scheme of oligonucleotide is shown in the below-mentioned Reaction Scheme IV.

Reaction Scheme IV

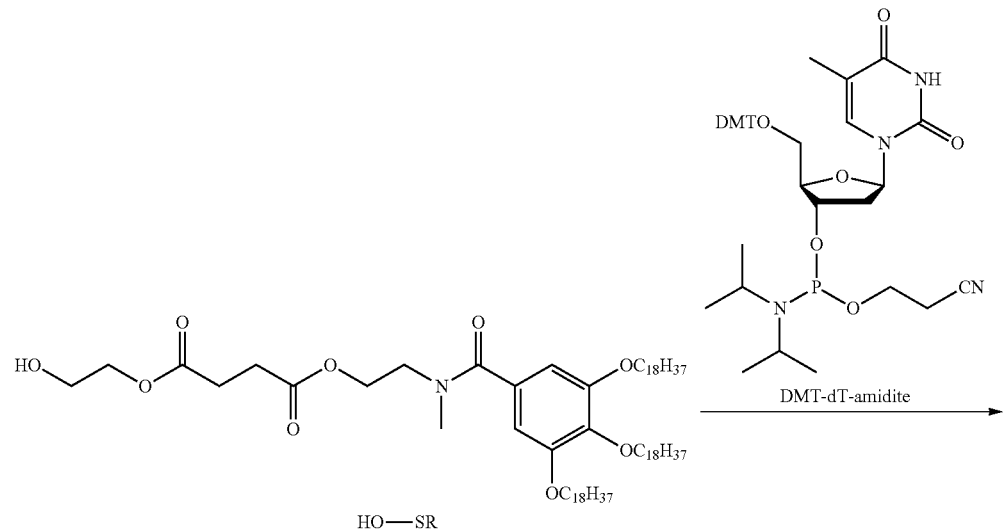

51 52
-continued
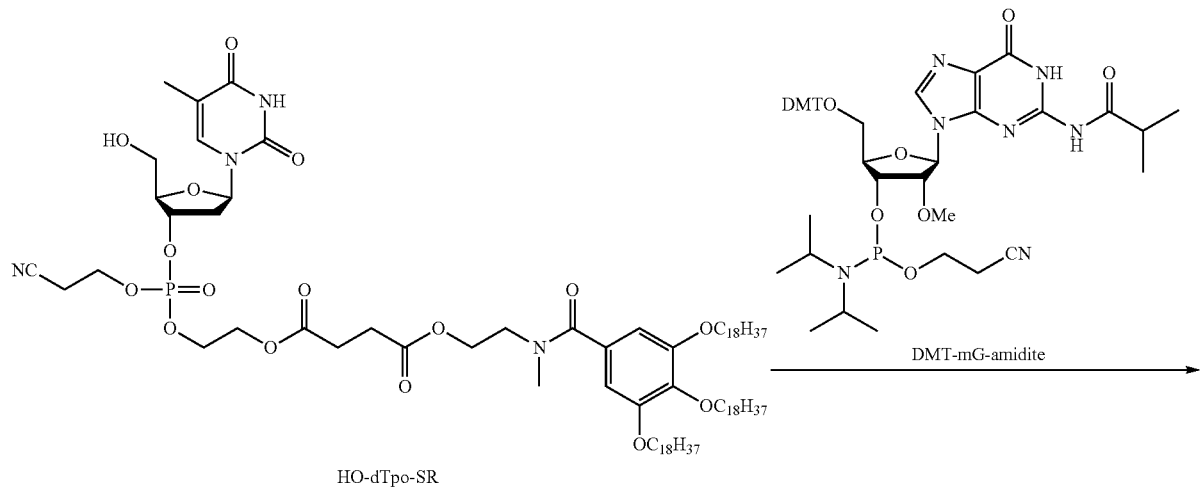
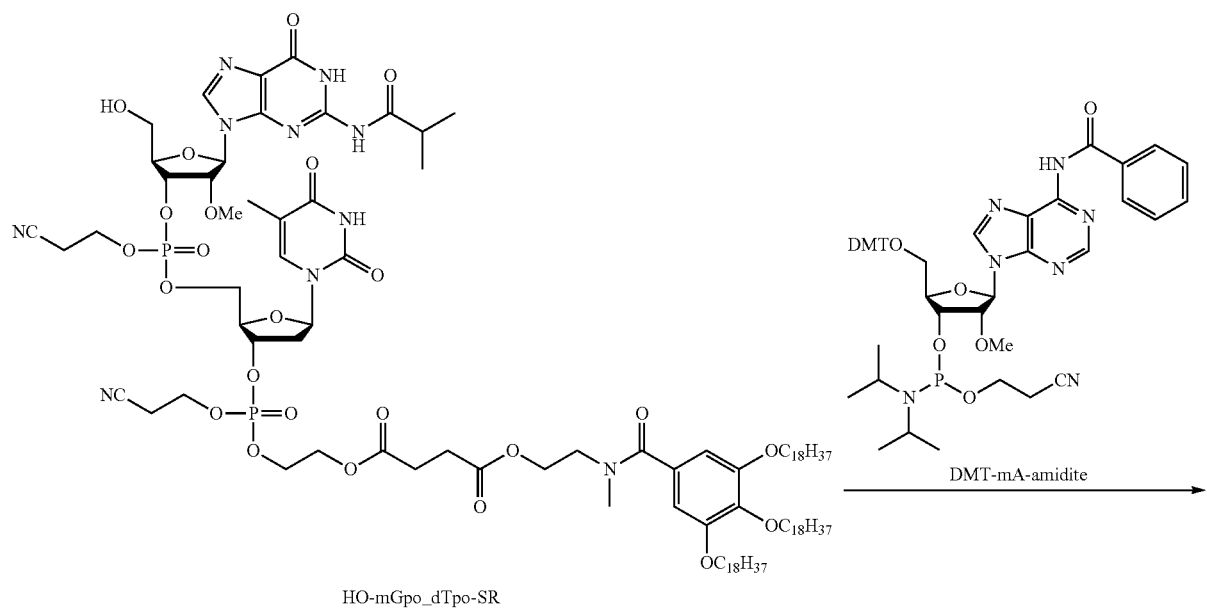

-continued

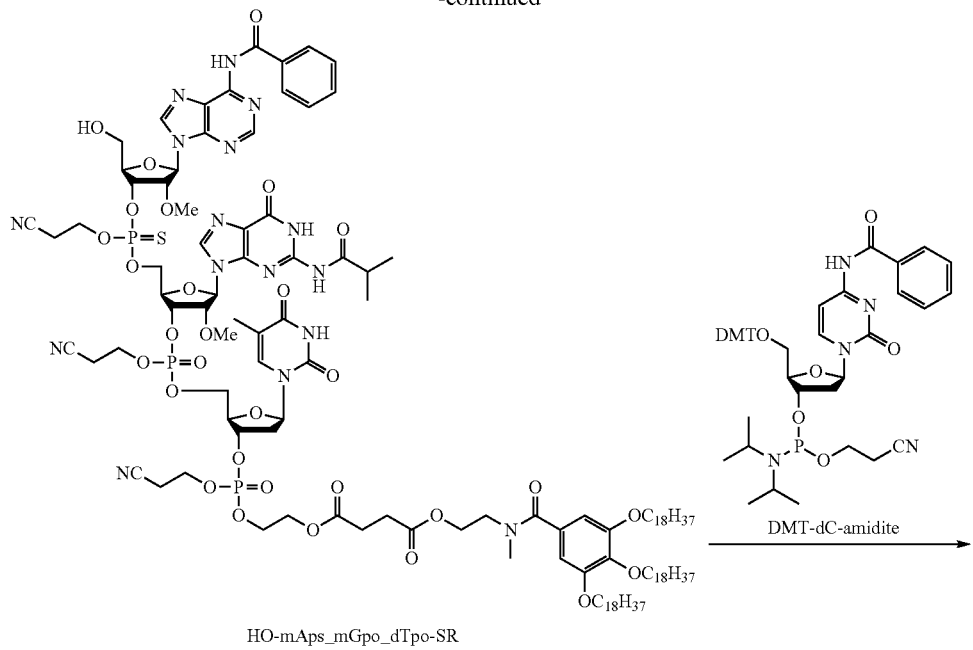

HO-mAps_mGpo_dTpo-SR

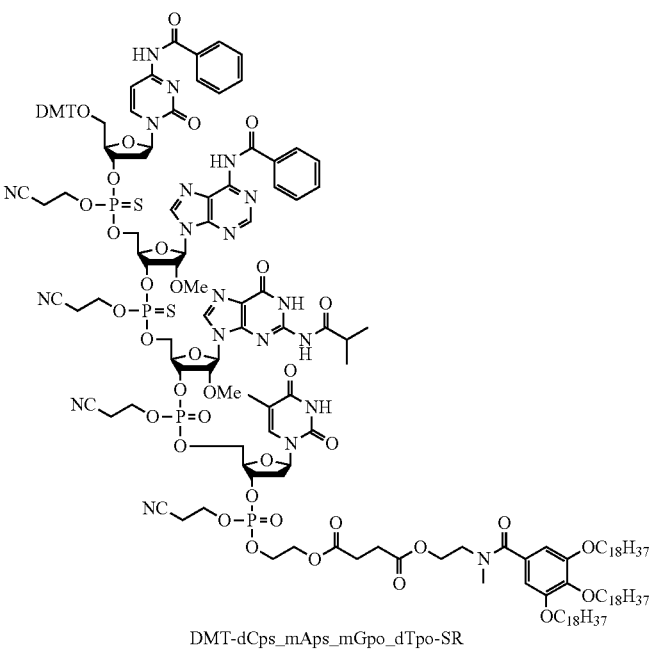

DMT-dCps_mAps_mGpo_dTpo-SR

Synthesis of Compound HO-dTpo-SR

To a 2-hydroxyethyl 2-(N-methyl-3,4,5-tris(octadecyl) benzamide)ethyl succinate 3.39 g in a 200 mL round-bottom flask were added dehydrated dichloromethane 60 mL and the compound DMT-dT-amidite 3.35 g, and the mixture was solubilized, and after the solubilization, to the solubilized solution was added ETT 879 mg, and the mixture was stirred at room temperature for 30 minutes. After 15 minutes, the disappearance of the substrates was determined by TLC. To the reaction solutions was added 2-cyanoethyl octadecyl diisopropyl phosphoramidite 424 µL, and the reaction mixture was stirred for 15 minutes. To the reaction mixture was added ethanol 876 µL, and the mixture was stirred at room temperature for 10 minutes. To the mixture were added a mixed solution of pyridine:acetonitrile=6:4 (v/v) (30 mL) and 2-butanone peroxide (0.1 M dichloromethane solution) 81 mL, and the mixture was stirred at room temperature for 15 minutes. To the reaction mixture was added trimethyl phosphite 658 µL, and the mixture was further stirred for 15 minutes. The resulting reaction mixture was diluted with dichloromethane, and thereto was then added methanol 150 mL, and the mixture was concentrated under reduced pressure. The resulting solids were filtered, and washed with methanol to obtain an intermediate compound DMT-dTpo-SR.

The resulting intermediate compound DMT-dTpo-SR was solubilized into dichloromethane 225 mL in a 500 mL round-bottom flask, and thereto were added pyrrole 5.2 mL and dichloroacetic acid 7.4 mL. The mixture was stirred at room temperature for 15 minutes, and thereto were then added methanol 150 mL and pyridine 8.70 mL. The mixture was concentrated under reduced pressure, and the resulting solids were filtered, washed with methanol and dried under reduced pressure to HO-dTpo-SR as a desired product 4.38 g. $^1$H-NMR (400 MHz CDCl$_3$); δ 0.88 (t, 9H, J=7.2 Hz), 1.2-1.4 (m, 84H), 1.4-1.5 (m, 6H), 1.60 (s, broad, 1H), 1.71-1.81 (m, 6H), 1.91 (s, 3H), 2.47-2.54 (m, 2H), 2.64-2.71 (m, 4H), 2.80 (t, 2H, J=6.0 Hz), 3.05 (s, 3H), 3.65-3.81 (m, 2H), 3.84-3.88 (m, 2H), 3.93-3.97 (m, 6H), 4.23-4.40 (m, 9H), 5.12-5.18 (m, 1H), 6.23 (t, 1H, J=6.8 Hz), 6.58 (s, 2H), 7.52 (s, 1H), 8.14-8.18 (m, 0.5H), 8.52-8.58 (m. 0.5H)
$^{31}$P-NMR (162 MHz CDCl$_3$); δ −3.15, −3.07

Synthesis of Compound HO-mGpo-dTpo-SR

To the compound HO-dTpo-SR 1.49 g in a 100 mL round-bottom flask were added dehydrated dichloromethane 20 mL and the compound DMT-mG-amidite 1.33 g, and the mixture was solubilized, and to the solubilized solution was added ETT 293 g, and the mixture was stirred at room temperature overnight. The disappearance of the substrate was determined by TLC. To the reaction solution was added 2-cyanoethyl octadecyl diisopropyl phosphoramidite 141 µL, and the reaction mixture was stirred for 30 minutes. To the reaction mixture was added ethanol 292 µL, and the mixture was stirred at room temperature for 10 minutes. To the reaction mixture was added 2-butanone peroxide (6.5 M) 0.55 mL, and the mixture was stirred at room temperature for 15 minutes. To the reaction mixture was added trimethyl phosphite 328 µL, and the mixture was further stirred for 15 minutes. The resulting reaction mixture was diluted with dichloromethane 55 mL, and thereto were added pyrrole 1.7 mL and trifluoroacetic acid 2.3 mL. The mixture was stirred at room temperature for 15 minutes, and thereto were then added methanol 50 mL and pyridine 4.8 mL. The mixture was concentrated under reduced pressure, and the resulting solids were filtered, washed with methanol, and dried under reduced pressure to obtain the desired product HO-mGpo-dTpo-SR 2.00 g (yield: quantitative).

Synthesis of Compound HO-mAps-mGpo-dTpo-SR

To the compound HO-mGpo-dTpo-SR 2.00 g (max. 1.00 mmol) in a 100 mL round-bottom flask were added dehydrated dichloromethane 20 mL, and the compound DMT-mA-amidite 1.35 g under argon atmosphere, and the mixture was solubilized, and to the solubilized solutions was added ETT 293 mg, and the mixture was stirred at room temperature overnight. The disappearance of the substrate was determined by TLC. To the reaction solutions was added 2-cyanoethyl octadecyl diisopropyl phosphoramidite 141 µL, and the reaction mixture was stirred for 30 minutes. To the reaction mixture was added ethanol 292 µL, and the mixture was stirred at room temperature for 10 minutes. To the mixture were added 2,4,6-colidine 714 µL and DDTT 582 mg, and the mixture was stirred at room temperature for 45 minutes. To the reaction mixture was added trimethyl phosphite 328 µL, and the mixture was further stirred for 15 minutes. The resulting reaction mixture was diluted with dichloromethane 55 mL, and thereto were then added pyrrole 1.7 mL and trifluoroacetic acid 2.3 mL. The mixture was stirred at room temperature for 15 minutes, and thereto were then added methanol 50 mL and pyridine 4.8 mL. The mixture was concentrated under reduced pressure, and the resulting solids were filtered, washed with methanol, and concentrated under reduced pressure to obtain the desired compound HO-mAps-mGpo-dTpo-SR 2.42 g.

Synthesis of Compound DMT-dCps-mAps-mGpo-dTpo-SR

To the compound HO-mAps-mGpo-dTpo-SR 2.42 g in a 100 mL round-bottom flask were added dehydrated dichloromethane 20 mL and the compound DMT-dc-amidite 1.27 g under argon atmosphere, and to the solubilized solution was added ETT 293 mg, and the mixture was stirred art room temperature, and after the disappearance of the substrate was determined by HPLC (about two hours), to the reaction solution was added 2-cyanoethyl octadecyl diisopropyl phosphoramidite 141 µL, and the reaction mixture was stirred for 30 minutes. After the reaction was completed, to the reaction mixture was added ethanol 292 µL, and the mixture was stirred at room temperature for 10 minutes. To the mixture were added a mixed solution of pyridine:acetonitrile=6:4 (v/v) (10 mL) and DDTT 554 mg, and the mixture was stirred at room temperature for 45 minutes. To the reaction mixture was added trimethyl phosphite 219 µL, and the mixture was further stirred for 15 minutes. The resulting reaction mixture was diluted with dichloromethane, and thereto was added methanol mL, and the mixture was concentrated under reduced pressure. The resulting solids were filtered, and washed with methanol to obtain the desired compound DMT-dCps-mAps-mGpo-dTpo-SR 3.15 g.

Deprotection of Compound DMT-dCps-mAps-mGpo-dTpo-SR and Determination of Purity of the obtained tetramer The compound DMT-dCps-mAps-mGpo-dTpo-SR 4 mg was added to a vial, and thereto was added 28% aqueous ammonia 500 µL, and the mixture was allowed to stand at 55° C. for 8 hours. As a result of HPLC analysis under a condition described in the below-mentioned Table 2, the purity thereof was 98.5%. MS (MALDI, TOF) Anal. Calc. for $C_{64}H_{77}N_{15}O_{28}P_5S_2$: 1691.35. Found 1691.52

HPLC Analysis Condition

TABLE 2

| | |
|---|---|
| Column | ODS-A S-5 µm/30 nm (YMC) 150 × 4.6 mm ID |
| Eluate A | 0.1M Triethylamine-acetic acid pH = 7.0 |
| Eluate B | Methanol |
| Gradient | Concentration of Eluate B 0 → 100% (40 min) |
| Flow rate | 0.5 mL/min |
| Temperature | 60° C. |

Structural Formula of DMT-dCps-mAps-mGpo-dTpo-SR
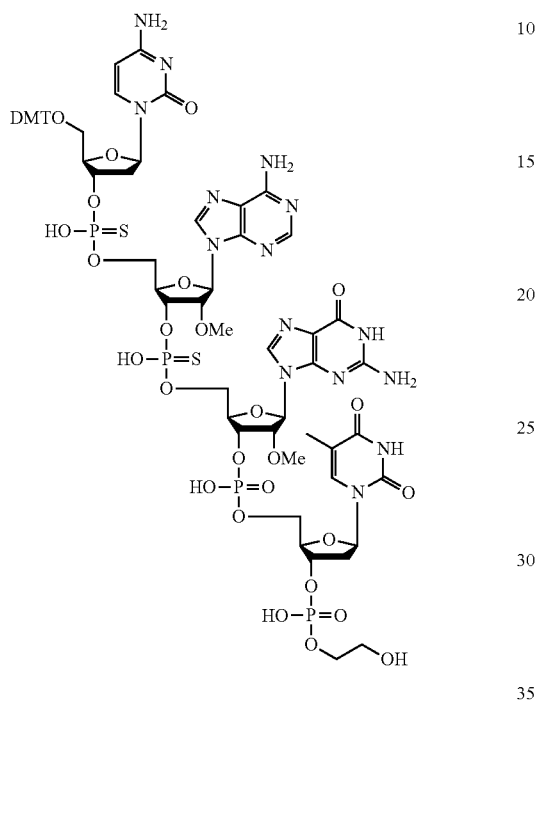
Example 11
Deposition of Guanine 6-Position O-Highly Liposoluble Amidite Adduct with Alcohol
The preparation of the guanine 6-position O-highly liposoluble amidite adduct is shown in the below-mentioned Reaction Scheme V.
Reaction Scheme V
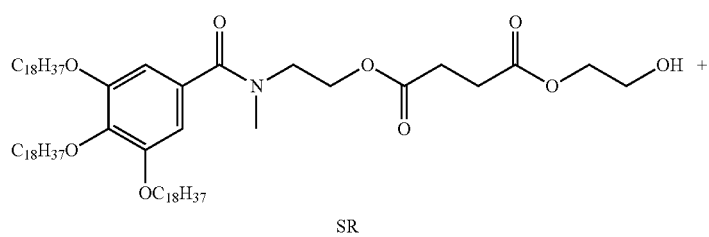
SR

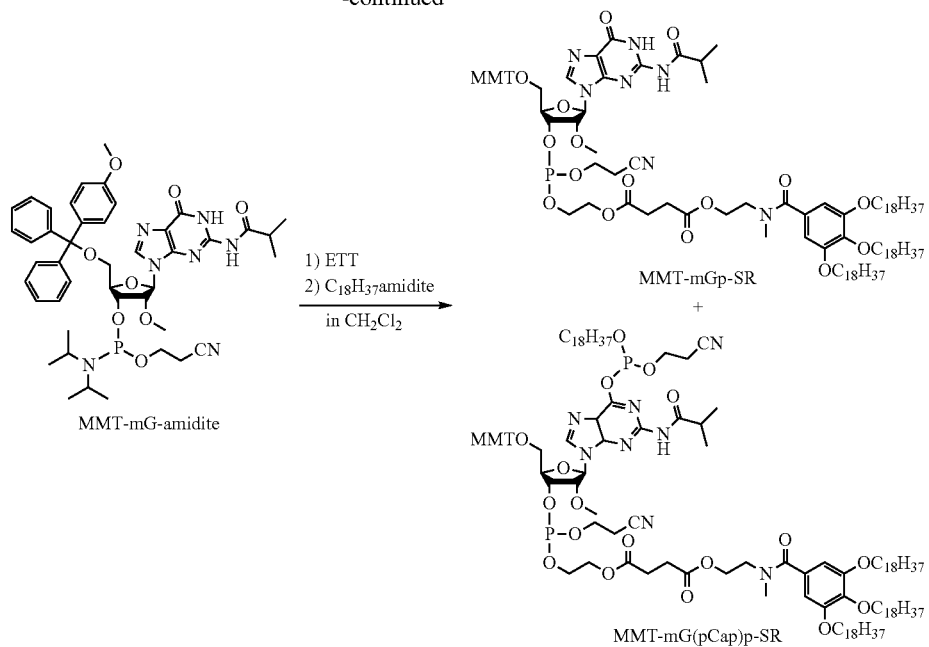
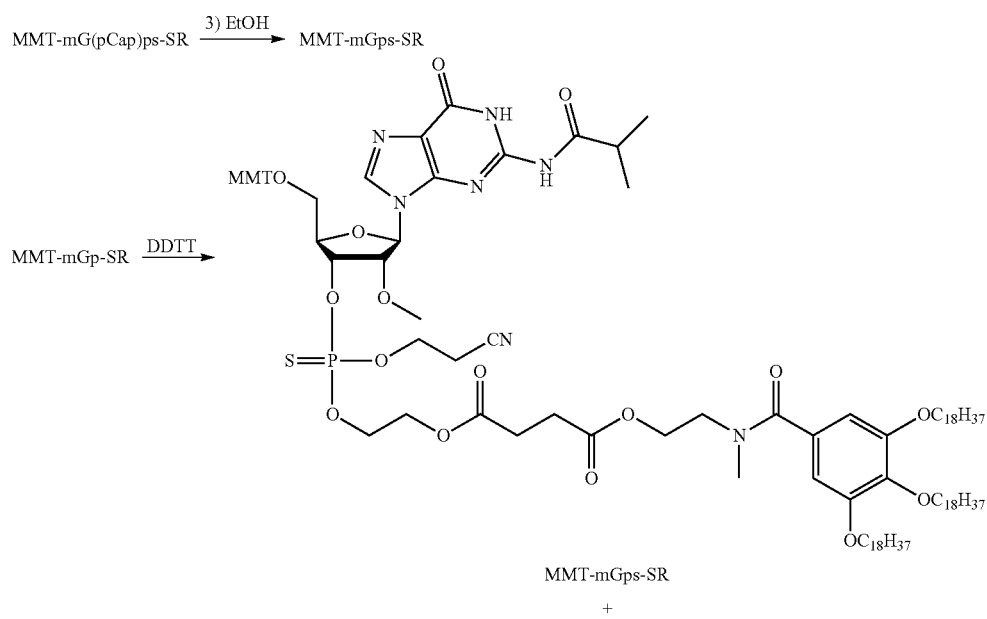

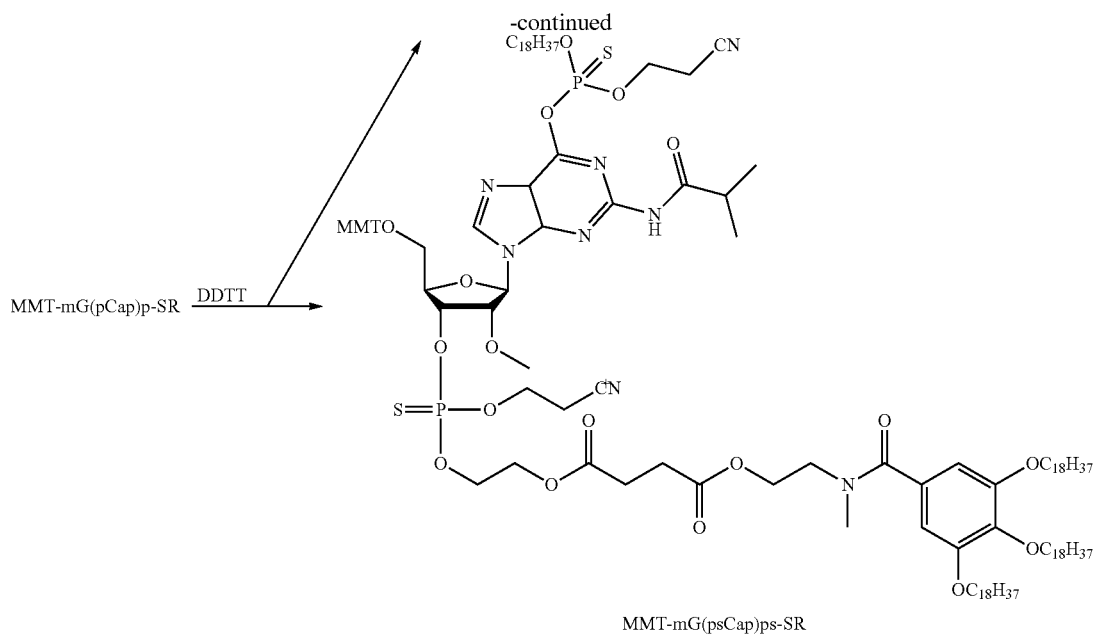

MMT-mG(psCap)ps-SR

Synthesis of Compound MMT-mGps-SR

To the 2-hydroxyethyl 2-(N-methyl-3,4,5-tris(octadecyl) benzamide)ethyl succinate 1.13 g in a 100 mL round-bottom flask were added dehydrated dichloromethane 20 mL and the compound MMT-mG-amidite 1.26 g under argon atmosphere, and the mixture was solubilized, and to the solubilized solution was added 5-ethylthio-4H-tetrazole (abbreviated ETT) 293 mg, and the mixture was stirred at room temperature overnight. The disappearance of the substrate was determined by TLC. To the reaction solution was added 2-cyanoethyl octadecyl diisopropyl phosphoramidite 141 μL, and the reaction mixture was stirred for 30 minutes. To the reaction mixture was added ethanol 292 μL, and the mixture was stirred at room temperature for 30 minutes. To the reaction mixture was added ethanol 292 μL, and the mixture was stirred at room temperature for 10 minutes, To the mixture were added a mixed solution of pyridine: acetonitrile 6:4 (v/v) and 3-((N,N-dimethylaminomethyl-idene)amino)-3H-1,2,4-dithiazole-5-thione (DDTT) 582 mg, and the mixture was stirred at room temperature for 45 minutes. To the reaction mixture was added trimethyl phosphite 218 μL (1.8 mmol), and the mixture was stirred at room temperature for 45 minutes. To the reaction mixture was added trimethyl phosphite 218 μL (1.8 mol), and after the mixture was further stirred for 15 minutes, and thereto was added methanol 50 mL. The mixture was concentrated under educed pressure, and the resulting solids were filtered, washed with methanol, and dried under reduced pressure, and the resulting solids were filtered, washed with methanol, and dried under reduced pressure to obtain the desired product MMT-mGps-SR 193 g.

$^1$H-NMR (400 MHz CDCl$_3$); δ 0.82-0.90 (m, 12H), 0.95-0.97 (m, 3H) 1.20-1.39 (m, 84H), 1.40-1.51 (m, 6H), 1.70-1.82 (m, 6H), 1.89-2.04 (m 1H), 2.57-2.70 (m, 5H), 2.72-2.89 (m, 1H), 3.05 (brs, 3H), 3.24-3.31 (m, 1H), 3.44 (s, 1.5H), 3.45 (s, 1.5H), 3.47-3.53 (m, 1H), 3.75-3.86 (m, 2H), 3.79 (s, 3H), 3.89-3.97 (m, 6H), 4.06-4.45 (m, 9H), 4.70-4.79 (m, 1H), 5.36-5.43 (m, 1H), 5.88 (d, 0.5H, J=6.8 Hz), 5.90 (d, 0.5H, J=8.0 Hz), 6.58 (s, 2H), 6.80-6.86 (m, 2H), 7.22-7.38 (m, 8H), 7.46-7.52 (m. 4H), 7.77 (s, 0.5H), 7.78 (s, 0.5H), 8.52 (brs, 0.5H), 8.61 (brs, 0.5H), 12.03 (s, 1H)

$^{31}$P-NMR (162 MHz CDCl$_3$); δ 67.85, 67.96

Synthesis of Mixture of Compound MMT-mGps-SR and Compound MMT-mG(psCap)ps-SR To a 2-hydroxyethyl 2-(N-methyl-3,4,5-tris(octadecyl) benzamide)ethyl succinate 0.56 g in a 100 mL round-bottom flask were added dehydrated dichloromethane 10 mL and the compound MMT-mG-amidite 0.63 g under argon atmosphere, and the mixture was solubilized, and to the solubilized solution was added ETT 146 mg, and the mixture was stirred at room temperature overnight. The disappearance of the substrate was determined by TLC. To the reaction solution was added ETT 98 mg, and thereto was added 2-cyanoethyl octadecyl diisopropyl phosphoramidite 353 μL, and the reaction mixture was stirred for 30 minutes. To the mixture were added a mixed solution of pyridine acetonitrile=6:4 (v/v) (5 mL) and DDTT 485 mg, and the mixture was stirred at room temperature for 45 minutes. To the reaction mixture was added trimethyl phosphite 137 μL, and after the mixture was stirred for 15 minutes, thereto was added methanol 25 mL. The mixture was concentrated under reduced pressure, and the resulting solids were filtered, washed with methanol, and dried under reduced pressure to a mixture of the compound MMT-mGps-SR and the compound MMT-mG(psCap)ps-SR 0.98 g.

Mixture of Compound MMT-mGps-SR and Compound MMT-mG(psCap)ps-SR $^{31}$P-NMR (162 MHz CDCl$_3$); δ 67.85, 67.96, 71.43

Next, a detrityl reaction scheme of the guanine 6-position O-highly liposoluble amidite adduct P (five valent) as prepared above with an acid is shown in the below-mentioned Reaction Scheme VI.

Reaction Scheme VI

MMT-mGps-SR →

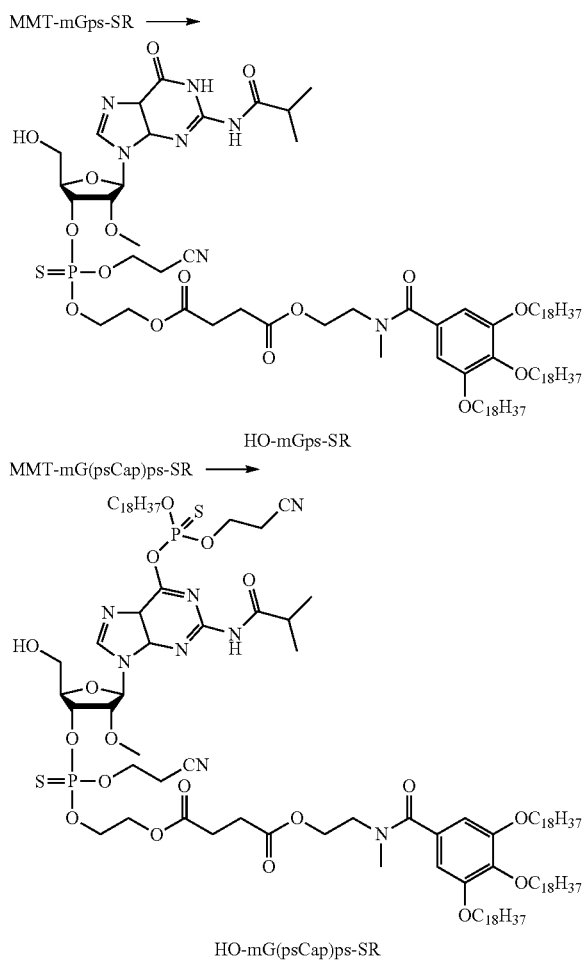

HO-mGps-SR

MMT-mG(psCap)ps-SR →

HO-mG(psCap)ps-SR

Synthesis of Compound HO-mGps-SR

A MMT-mGps-SR 0.380 g was solubilized into dichloromethane 15 mL in a 50 mL round-bottom flask, and thereto were added pyrrole 0.35 mL and trifluoroacetic acid 0.46 mL. The mixture was stirred at room temperature for 15 minutes, and thereto were then added methanol 10 mL and pyridine 0.97 mL. The mixture was concentrated under reduced pressure, and the resulting solids were filtered, and washed with methanol, and dried under reduced pressure to obtain the desired compound HO-mGps-SR 0.320 g.

$^1$H-NMR (400 MHz CDCl$_3$); δ 0.88 (t 9H, J=6.8 Hz) 1.19-1.39 (m, 90H), 1.40-1.51 (m, 6H), 1.70-1.82 (m, 6H), 1.89-2.04 (m 1H), 2.58-2.73 (m, 5H), 2.75-2.85 (m, 2H), 3.07 (brs, 3H), 3.38 (s, 1.5H), 3.39 (s, 1.5H), 3.52-4.06 (m, 10H), 4.12-4.42 (m, 8H), 4.42-4.49 (m, 1H), 4.53-4.58 (m, 1H), 5.32 (dd, 1H, J=10.8, 4.8 Hz), 5.87 (t, 1H, J=8.0 Hz), 6.58 (s, 2H), 7.90-7.96 (m, 1H), 8.80-8.96 (m, 1H), 12.13 (s, 1H)

$^{31}$P-NMR (162 MHz CDCl$_3$); δ 67.55

Synthesis of Mixture of Compound HO-mGps-SR and Compound HO-mG(psCap)ps-SR

A mixture of Compound HO-mGps-SR and Compound HO-mG(psCap)ps-SR 0.322 g was obtained from a mixture of the compound MMT-mGps-SR and the compound MMT-mG(psCap)ps-SR 0.380 g.

$^{31}$P-NMR (162 MHz CDCl$_3$); δ 51.81, 67.55, 67.13

Example 12

Observation of Deposition of Guanine 6-position 0-highly liposoluble amidite adduct with a nucleophile in a NMR tube Solution A: 0.057M MMT-mGps-SR in CDCl$_3$ solution, and Solution B: 0.9M ETT in in CDCl$_3$ solution were prepared.

A C$_{18}$H$_{37}$O-phosphoramidite 22.1 µL was dispensed into a NMR tube, and thereto was added the solution A 437.5 µL and after the mixture was mixed thoroughly, thereto was added the solution B 125 µL, and the mixture was stirred. At 5 minutes after the solution B was added, $^{31}$PNMR for the $^{31}$P signal specific to each of the below-mentioned compounds is measured.

An integrated value at 124.9 ppm of a signal derived from C$_{18}$H$_{37}$O-phosphoramidite ETT adduct An integrated value at 133.5 ppm of a signal derived from MMT-mG(pCap)ps-SR An integrated value at 146.6 ppm of a signal derived from C$_{18}$H$_{37}$O-phosphoramidite Each of the above-mentioned integrated values were made a numerator of quotient, and the integrated value at 68.5 ppm of a signal derived from MMT-mGps-SR were made a denominator, and the quotient value were then calculated, and at 5 minutes after adding the below-mentioned various nucleophiles (2 equivalents as opposite to a phosphoramidite) and stirring, a $^{31}$PNMR was measured, and the measured value was compared with the quotient value thereof, and the respective residual ratio thereof was calculated. In the case where an organic base, 2,4,6-collidine (3 equivalents) was added, they were added before adding various kinds of nucleophile is added, and the mixture was stirred.

The results are shown in Table 3.

TABLE 3

| | | C18H37O-amidite | mG(pCap) | Cap-ETT-adduct |
|---|---|---|---|---|
| | 2 eq MeOH | 2.7% | 13.9% | 19.2% |
| 3 eq colidine | 2 eq MeOH | 45.3% | 14.0% | 8.8% |
| | 2 eq EtOH | 0.0% | 0.0% | 0.0% |
| 3 eq colidine | 2 eq EtOH | 40.0% | 0.0% | 0.0% |
| | 2 eq CF3CH2OH | 0.0% | 0.0% | 0.0% |
| 3 eq colidine | 2 eq CF3CH2OH | 63.3% | 0.0% | 0.0% |
| | 2 eq N-HOSuc | | | |
| 3 eq colidine | 2 eq N-HOSuc | 48.1% | 80.1% | 54.8% |
| | 2 eq AcOH | | | |
| 3 eq colidine | 2 eq AcOH | 53.5% | 65.0% | 45.6% |
| | 2 eq H2O | 0.0% | 0.0% | 0.0% |
| 3 eq colidine | 2 eq H2O | 62.4% | 0.0% | 0.0% |

Each of acetic acid and N-hydroxysuccinimide was prepared as a mixed solution thereof with collidine respectively, which then was added.

As this result, in the case of all nucleophiles having low acidity, a disappearance of an efficient signal derived from mG(pCap) was confirmed. Also it was found that a signal derived from the mG(pCap) can be disappeared effectively in the state where an activation by ETT (acid) was weaken by adding an organic base 2,4,6-collidine in advance, which is found out that the present reaction is not a reaction where a nucleophile is worked as a quenching agent.

Example 13

Verification of a Residual Amount of N−1 Oligonucleotide by-Product and an Efficient of Sulfidation in the Presence of a Nucleophile by Capping A reaction scheme which investigates a suppression of a formation of N−1 oligonucleotide by-product by using a capping reagent and a retention of efficiency of sulfidation reaction by using a nucleophile is shown in the below-mentioned Reaction Scheme VII.

Reaction Scheme VII

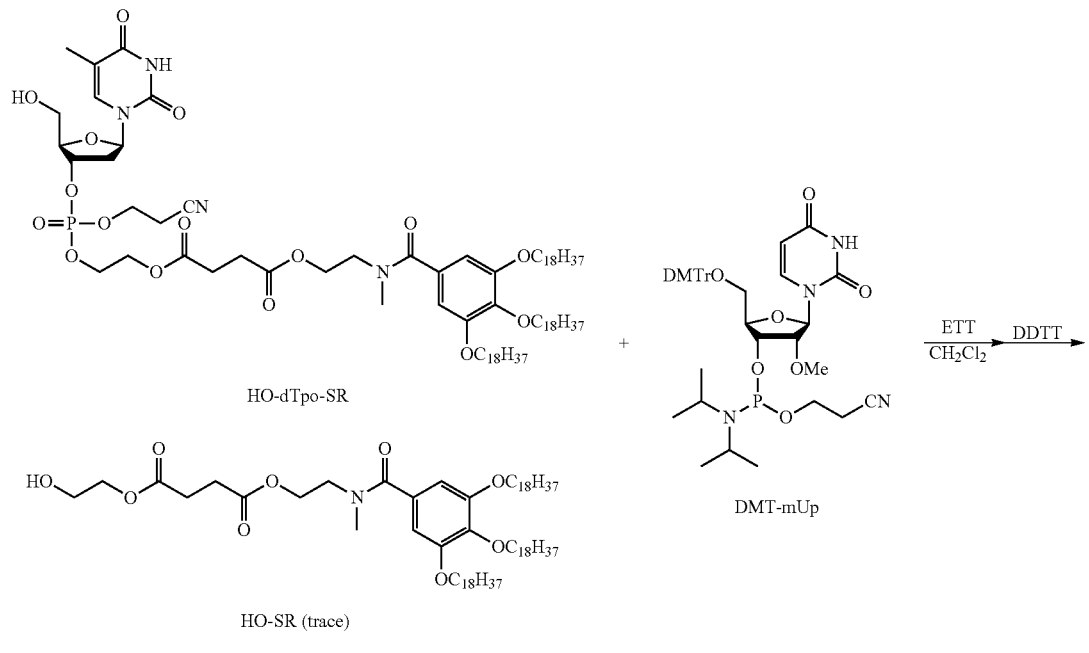

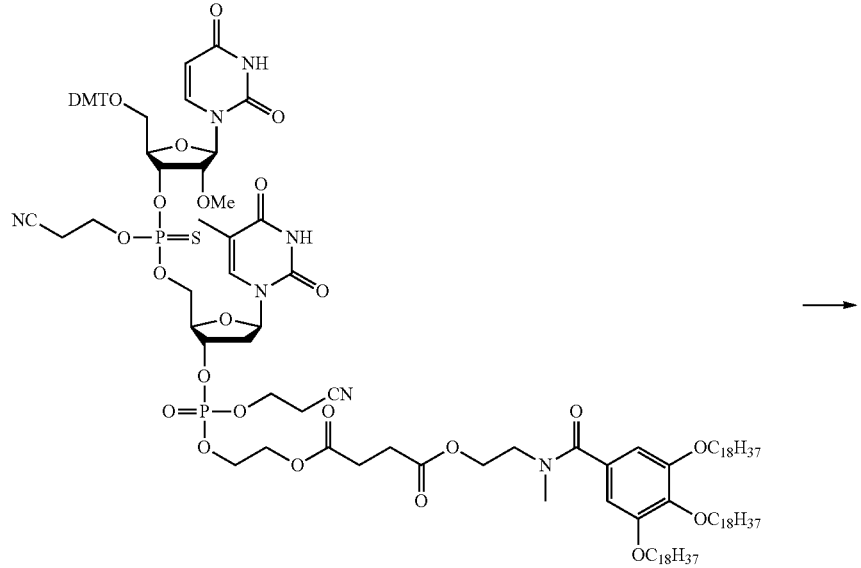

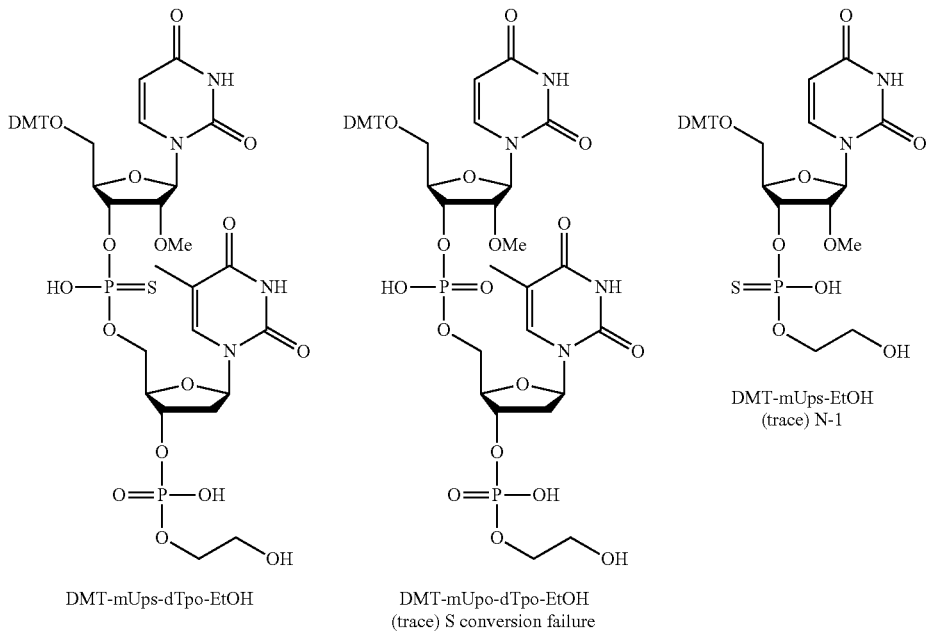

DMT-mUps-dTpo-EtOH | DMT-mUpo-dTpo-EtOH (trace) S conversion failure | DMT-mUps-EtOH (trace) N-1

To the compound HO-dTpo-SR 0.74 g in a 100 mL round-bottom flask were added dehydrated dichloromethane 10 mL and DMT-mU amidite 0.42 g under argon atmosphere, and to the solubilized solution was added ETT 122 mg, and the mixture was stirred at room temperature for 2 hours. To the reaction solution was added 2-cyanoethyl octadecyl diisopropyl phosphoramidite 71 μL, and the reaction mixture was stirred for 45 minutes. After the reaction was completed, to the reaction mixture was added ethanol 146 μL, and the mixture was stirred at room temperature for 10 minutes. To the mixture were added a mixed solution of pyridine acetonitrile=6:4 (v/v) (5 mL) and DDTT 335 mg, and the mixture was stirred at room temperature for 15 minutes. To the reaction mixture was added trimethyl phosphite 133 μL, and the mixture was further stirred for 15 minutes. The resulting reaction mixture was diluted with dichloromethane, and thereto was then added methanol 27 mL, and the mixture was concentrated under reduced pressure. The resulting solids were filtered and washed with methanol to obtain DMT-mUps-dTpo-SR 1.08 g.

The compound DMT-mUps-dTpo-SR 4 mg was added to a vial, and thereto was added 28% aqueous ammonia 500 μL, and the mixture was allowed to stand at 55° C. for 8 hours to form a solution of DMT-mUps-dTpo-EtOH, and the efficiency of sulfidation and N-1 production amount of the obtained solution was determined with HPLC by using as a reference standard DMT-mUpo-dTpo-EtOH and DMT-dTps-EtOH that are synthesized separately by nucleic acid synthesizer. As a result, the production amounts of DMT-mUpo-dTpo-EtOH and DMT-dTps-EtOH (N-1 by-product) were both below 0.1% as opposed to the desired sulfidation product DMT-mUps-dTpo-EtOH. As a result, it was found that an efficiency of sulfidation wasn't declined by an addition of ethanol, and a N-1 formation was suppressed efficiently by an addition of a capping reagent.

Example 14

Validation of Diacylation of Adenine Base by Capping with Acetic Anhydride

The reaction scheme for investigating a formation of diacylated adenine base by using capping with acetic anhydride is shown in the below-mentioned reaction scheme VIII.

Reaction Scheme VIII

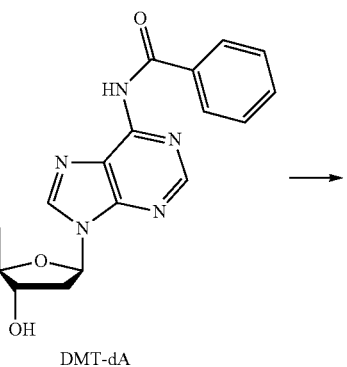

DMT-dA

69

-continued

DMT-dA-Suc

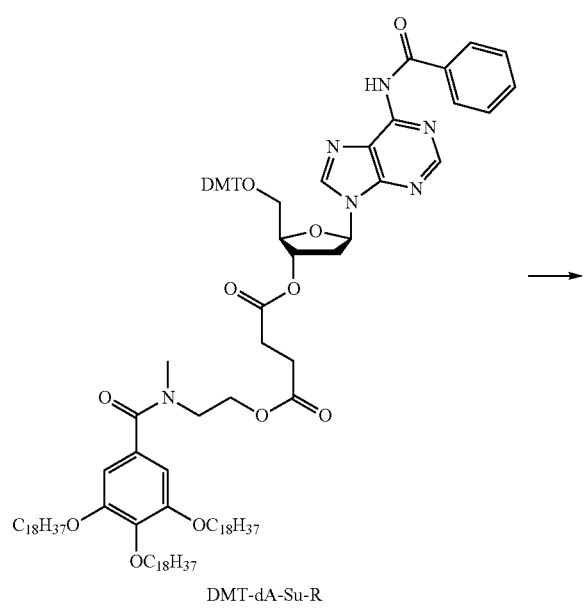

DMT-dA-Su-R

70

-continued

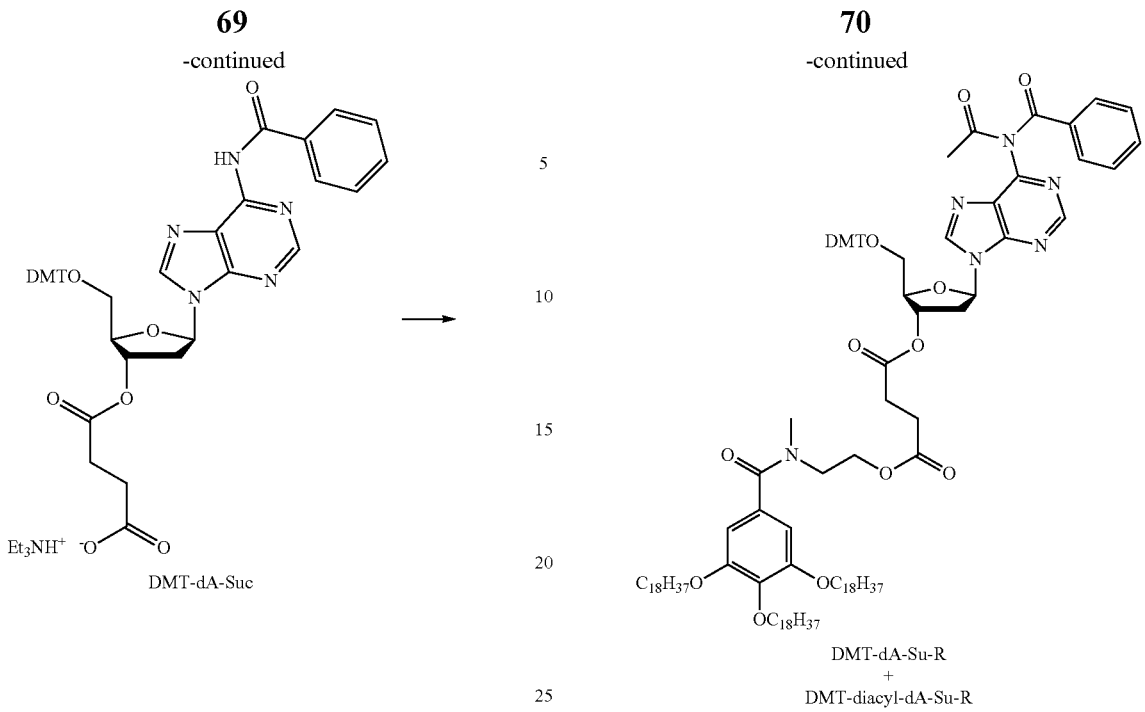

DMT-dA-Su-R
+
DMT-diacyl-dA-Su-R

Synthesis of Compound DMT-dA-Suc

The compound DMT-dA 13.2 g (manufactured by carbo-synth Ltd.) was solubilized into dehydrated dichloromethane 100 mL, and to the solutions were added triethylamine 8.4 mL and succinic anhydride 3.0 g. The mixture was stirred at room temperature overnight, and to the reaction mixture was added methanol 2.0 mL, and the mixture was further stirred at room temperature s overnight. The resulting mixture solutions was washed with phosphate triethylamine buffer (pH about 6.8), and the mixture solutions were concentrated under reduced pressure, and then distilled under reduced pressure overnight to remove any volatile components and also obtain DMT-dA-Suc 17.7 g. The existence ratio of triethylamine was approximated from $^1$H NMR integrated value.

$^1$H-NMR (400 MHz CDCl$_3$); δ 1.19 (t, 9H, J=7.2 Hz), 2.54-2.75 (m, 5H), 2.92 (q, 6H, d=7.2), 2.96-3.05 (m, 1H), 3.38-3.49 (m, 1H), 3.74 (s, 6H) 4.33-4.38 (m, 1H), 5.52-5.58 (m, 1H), 6.53 (dd, 1H, J=8.4, 5.2 Hz), 6.75-6.83 (m, 4H), 7.16-7.32 (m, 5H), 7.36-7.41 (m. 2H), 7.50-7.56 (m. 2H), 7.57-7.64 (m. 1H), 8.00-8.06 (m. 2H), 8.19 (s. 1H), 8.73 (s. 1H), 9.03 (brs. 1H)

Synthesis of Compound DMT-dA-Su-R

To the compound III 15.7 g and the compound DMT-dA-Suc 17.7 g was added dehydrated chloroform 100 mL, and to the mixture solutions were further added diisopropylethylamine 4.33 mL, HBTU 9.42 g and DMAP 3.04 g. The mixture was stirred at 45° C. overnight. To the resulting reaction mixture was added methanol 100 mL, and the mixture was concentrated under reduced pressure. The resulting solids were filtered, washed with methanol, and dried under reduced pressure to obtain the compound DMT-dA-Su-R as a solid 27.9 g.

$^1$H-NMR (400 MHz CDCl$_3$); δ 0.88 (t, 9H, J=6.4 Hz), 1.20-1.38 (m, 84H), 1.41-1.50 (m, 6H), 1.68-1.84 (m, 6H), 2.62-2.74 (m, 5H), 2.99-3.12 (m, 4H), 3.42-3.52 (m, 3H), 3.68-3.79 (m, 1H) 3.79 (s, 6H), 3.92-3.98 (m, 6H), 4.10-4.51 (m, 3H), 5.53-5.62 (m, 1H), 6.52 (dd, 1H J=8.4, 5.6 Hz), 6.58 (s, 2H), 6.74-6.84 (m, 4H), 7.16-7.31 (m, 5H), 7.34-7.41 (m. 2H), 7.50-7.58 (m. 2H), 7.59-7.65 (m. 1H), 8.00-8.06 (m. 2H), 8.18 (s. 1H), 8.74 (s. 1H), 8.94 (brs. 1H)

Synthesis of a Mixture of Compound DMT-Diacyl-dA-Su-R, and Compound DMT-dA-Su-R

To DMT-dA-Su-R 27.9 g was added dehydrated chloroform 100 mL, and further 2,4,6-trimethyl pyridine 45 mL, 1-methylimidazole 30 mL, and acetic anhydride 30 mL, and the mixture was stirred overnight. To the resulting reaction mixture was added methanol 100 mL, and the mixture was concentrated under reduced pressure. The resulting solids were solids were filtered, washed with methanol, and dried under reduced pressure to obtain a mixture of the compound DMT-diacyl-dA-Su-R and the compound DMT-dA-Su-R 27.8 g.

NMR comparison figures of a mixture of the compound DMT-diacyl-dA-Su-R and the compound DMT-dA-Su-R (upper column) and the compound DMT-dA-Su-R (lower column) are shown in FIG. 2.

It was found to be a mixture of the compound DMT-diacyl-dA-Su-R which was diacylated in about 80% and the raw compound DMT-dA-Su-R in about 20%, and a mixture containing a diacylated product on adenine base was formed by a capping with acetic anhydride. It can be easily predicted from these findings that as the oligonucleotide chain length increases, the constitute composition of the oligonucleotide product becomes more complicated. As a result, it was found that when a capping step with acetic anhydride is introduced in a preparation of oligonucleotide by liquid phase method using a pseudo solid phase protecting group, a confirmation of reaction endpoint in a coupling step, which is, a confirmation of reaction efficiency became difficult.

INDUSTRIAL APPLICABILITY

Using a solution containing a highly liposoluble phosphoramidite obtained by a preparation method of highly liposoluble phosphoramidite compound of the present invention, or a composition comprising the same solution and optionally an additive as a capping reaction reagent can produce high-purity (oligo)nucleotide with a convenient procedure on a large scale. Also the preparation method of the oligonucleotide of the present invention can produce a high-purity oligonucleotide on a large scale.

The invention claimed is:

1. A method for preparing a compound represented by formula (I):

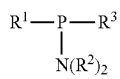

[wherein,
$R^1$ represents an optionally substituted C6-C30 alkyloxy group, and the substituent is at least one group selected from a C1-C3 alkyl group or a C3-C6 cycloalkyl group, $R^2$ each independently represents an optionally substituted C1-C6 alkyl group, and the substituent is at least one group selected from a C1-C3 alkyl group or a C3-C6 cycloalkyl group, and $R^3$ represents an optionally substituted C6-C30 alkyloxy group, an optionally substituted C1-C8 alkyloxy group, or an optionally substituted C2-C8 alkynyloxy group, and the substituent in the optionally substituted C6-C30 alkyloxy group is at least one group selected from a C1-C3 alkyl group, or a C3-C6 cycloalkyl group, and the substituent in the optionally substituted C1-C8 alkyloxy group or the optionally substituted C2-C8 alkynyloxy group is a cyano group (CN)], which comprises the following steps:
(1) reacting an aliphatic alcohol and a trivalent phosphorus compound in organic solvent in the presence of an activator or an organic base;
(2) washing the resulting reaction mixture with water in a separatory funnel;
(3) recovering the organic layer after the step (2) and concentrating it (with the proviso that when the organic solvent used in the step (1) is a nitrile solvent, the steps (2) to (3) may be omitted);
(4) solubilizing the resulting residue obtained in the step (3) in an aliphatic hydrocarbon solvent (with the proviso that when the organic solvent used in the step (1) is an aliphatic hydrocarbon solvent, the steps (2) to (3) may be omitted);
(5) washing the aliphatic hydrocarbon solution prepared in the step (4) with a nitrile solvent in a separatory funnel;
(6) recovering the aliphatic hydrocarbon solution after the step (5) to obtain a solution of a phosphoramidite compound.

2. The method according to claim 1 wherein the aliphatic hydrocarbon solvent used in the step (4) is at least one selected from pentane, hexane, heptane or octane, and the nitrile solvent used in the step (5) is at least one selected from acetonitrile, propionitrile, or benzonitrile.

3. The preparation method according to claim 1 wherein $R^1$ represents an optionally substituted C10-C30 primary or secondary alkyloxy group, and $R^3$ represents a —OCH$_2$CH$_2$CN, —OCH$_3$ or —OCH$_2$CH$_3$ group.

4. The preparation method according to claim 1 wherein each $R^2$ represents a i-propyl group.

5. The preparation method according to claim 1 wherein the compound represented by formula (I) is a compound represented by the following formula:

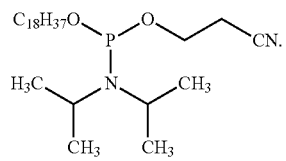

6. The preparation method according to claim 1 wherein the solution obtained in the step (6) is a solution of a substantially pure phosphoramidite compound which does not contain H-phosphonate compound and a diamidite compound.

* * * * *